(12) United States Patent
Balasubramanian et al.

(10) Patent No.: US 8,263,648 B2
(45) Date of Patent: Sep. 11, 2012

(54) DIEBENZOFURAN DERIVATIVES AS INHIBITORS OF PDE-4 AND PDE-10

(75) Inventors: Gopalan Balasubramanian, Secundarabad (IN); Ravi Dhamjewar, Hyderabad (IN); Shrikant Havale, Hyderabad (IN); Sreedhara Swamy Keshavapura Hosamane, Mumbai (IN)

(73) Assignee: Mylan Laboratories Ltd., Hyderabad (IN)

( * ) Notice: Subject to any disclaimer, the term of this patent is extended or adjusted under 35 U.S.C. 154(b) by 591 days.

(21) Appl. No.: 12/440,810

(22) PCT Filed: Sep. 10, 2007

(86) PCT No.: PCT/IB2007/002596
§ 371 (c)(1), (2), (4) Date: Mar. 11, 2009

(87) PCT Pub. No.: WO2008/032171
PCT Pub. Date: Mar. 20, 2008

(65) Prior Publication Data
US 2009/0281131 A1 Nov. 12, 2009

(30) Foreign Application Priority Data

Sep. 11, 2006 (IN) .......................... 1647/CHE/2006

(51) Int. Cl.
*A01N 43/08* (2006.01)
*A61K 31/34* (2006.01)
*C07D 307/91* (2006.01)
(52) U.S. Cl. ....................... 514/468; 549/460
(58) Field of Classification Search .................. 549/457, 549/460; 514/468
See application file for complete search history.

(56) References Cited

FOREIGN PATENT DOCUMENTS
WO WO 2006011024 A2 * 2/2006

OTHER PUBLICATIONS

Vippagunta et. al., Advanced Reviews Drug Delivery, 2001, Elsevier, vol. 48, pp. 3-26.*
Friese et. al., Brain, 2006, Oxford University Press, vol. 129, pp. 1940-1952.*
Cho et. al., Pharmacological Research, 2004, Academic Press, vol. 49, pp. 423-431.*
McCluskie et. al., The Journal of Pharmacology and Experimental Therapeutics, 2006, The American Society for Pharmacology and Experimental Therapeutics, vol. 319, issue 1, pp. 468-476.*

* cited by examiner

*Primary Examiner* — Sreeni Padmanabhan
*Assistant Examiner* — Sarah Pihonak
(74) *Attorney, Agent, or Firm* — Ladas & Parry LLP

(57) ABSTRACT

The present invention relates to novel heterocyclic compounds that are useful as phosphodiesterase inhibitors (PDEs) in particular phosphodiesterase type 4 (PDE IV) inhibitors and phosphodiesterase type 10 (PDE 10) inhibitors, processes for their preparation, pharmaceutical compositions containing them and their use in treating allergic and inflammatory diseases as well as for inhibiting the production of Tumor Necrosis Factor (TNF-α).

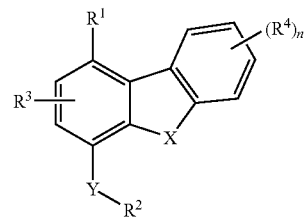

20 Claims, No Drawings

DIEBENZOFURAN DERIVATIVES AS INHIBITORS OF PDE-4 AND PDE-10

This application claims priority to Indian patent application No. 1647/CHE/2006 filed on Sep. 11, 2006, the contents of which are incorporated by reference in their entirety

FIELD OF INVENTION

The present invention relates to novel heterocyclic compounds that are useful as phosphodiesterase inhibitors (PDEs) in particular phosphodiesterase type 4 inhibitors (PDE-4) and type 10 inhibitors (PDE-10) represented by formula (I), their derivatives, analogs, tautomeric forms, stereoisomers, bioisosters, diastereomers, polymorphs, enantiomers, appropriate N-oxides, pharmaceutically acceptable salts, pharmaceutically acceptable hydrates pharmaceutically acceptable solvates, pharmaceutically acceptable compositions containing them and their use in treating allergic and inflammatory diseases and for inhibiting the production of Tumor Necrosis Factor (TNF-α).

In another aspect of the present invention, the compounds represented by general formula I are useful in the treatment of various allergic and inflammatory diseases including asthma, COPD, allergic rhinitis, allergic conjunctivitis, respiratory distress syndrome, chronic bronchitis, nephritis, rheumatoid spondylitis, osteoarthritis, atopic dermatitis, eosinophilic granuloma, psoriasis, rheumatoid septic shock, ulcerative colitis, parkinson's disease; multiple sclerosis, chronic inflammation, Crohn's syndrome (Nature Medicine, 1, 211-214 (1995) and ibid., 244-248 herein incorporated by reference in their entirety) also other inflammatory conditions of lungs, eyes, joints, bowels, skin, heart and central nervous system (CNS).

The present invention also relates to a process for the preparation of the novel heterocyclic compounds of the generic formula (I).
WI:mr

BACKGROUND OF THE INVENTION

Bronchial asthma is a complex multifactorial disease characterized by hyperactivity of the respiratory tract to external stimuli. Airway inflammation leads to a number of severe lung diseases including Asthma and chronic obstructive pulmonary diseases (COPD also known as Chronic Obstructive Airway Disease, Chronic Obstructive lung Disease or chronic airflow limitation and chronic airflow obstruction). The airflow limitation is usually progressive and associated with abnormal inflammatory response of the lungs to noxious particles or gases.

Many biological responses are mediated by levels of cyclic nucleotides mainly cAMP and cGMP which in turn are synthesized by adenylyl cyclases (ACs) and guanylate cyclases (GCs). To regulate levels of cAMP and cGMP, all cells have Phosphodiesterases (PDEs) that hydrolyze cAMP and cGMP to 5'-AMP and 5'-GMP. In humans there are 21 different PDE isoforms that are classified into 11 different groups. Basically these PDEs fall into three categories: 1. those that are specific to cAMP, 2. Those that are specific to cGMP and 3 those that act on both cAMP and cGMP. These 11 groups of PDEs are classified according to their nucleotide selectivity. PDE4 has 4 isoforms and in all the isoforms upstream conserved regions (UCRs) are present which appear to modulate dimerisation and may bind to signaling molecules such as lipids. There are at least 18 different splice variants of the four PDE4 isoforms. Because of the critical role of cAMP in mediating cytokine responses cAMP PDEs are also implicated. Many of the mediators of inflammatory response such as T cells, B cells, monocytes, neutrophils, eosinophils and macrophages have PDE4 enzymes as their primary cAMP PDE. Among the inflammatory diseases that are implicated by these cellular mediators are asthma, chronic obstructive pulmonary diseases (COPD), rheumatoid arthritis, inflammatory bowel disease, crohn's disease and multiple sclerosis. Consequently the development of PDE4 inhibitors as therapeutic agents for these diseases has been a major pharmaceutical focus. PDE4 indirectly controls the degree of bronchodilation. In the inflammatory cells cAMP is a negative regulator of the primary activating pathways such as cytokine release by T-cells. Inhibition of the PDE4 isozymes in these cells results in elevated cAMP levels and consequent inactivation of the inflammatory response. In addition to the direct role of cAMP in inflammatory cell function, elevated cAMP levels also lead to smooth muscle relaxation. Consequently, inhibition of PDE4 activity leading to higher cAMP levels cause bronchodilation thereby alleviating symptoms of respiratory diseases such as asthma or COPD.

Also Inhibition of PDE-IV enzyme increase levels of cAMP and Cyclic AMP modulates the activity of the most of the cells that contribute to the pathophysiology of allergic asthma. Elevation of cAMP would produce beneficial effects, some of which includes apart from airway smooth muscle relaxation, inhibition of mast cell mediator release, suppression of neutrophil degranulation, inhibition of basophil degranulation and inhibition of monocyte and macrophage activation. The connection between PDE4 activity and cognition has been speculated ever since the discovery that the cAMP-regulating dunce gene of the fruit fly encodes a PDE4 homologue (*Nature*, 1981, 289, 5793, 79-1; *J. mol. biol.*, 1991, 222, 3, 553-565). Another two important roles for PDE4D have recently been identified in cardiovascular tissue; one is a correlation for PDE4 polymorphism with stroke and another is an involvement in vascular smooth muscle cell proliferation (*Mol. Pharmacol.* 2005, 68, 3, 596-605). Finally, there are reports linking between PDE4D and osteoporosis. Specifically single nucleotide polymorphisms mapping to the PDE4D gene are linked to variability in bone mineral density (*BMC Med. Genet*, 2005, 6, 1, 9).

Inflammatory leukocytes infiltrate the airways of asthmatic patients in which eosinophils are the major component and also they are accumulated more in the lungs. When activated they synthesize and release inflammatory cytokines such as Interleukine-1, Interleukine-2 and Tumor Necrosis Factor-α (TNF-α) as well as inflammatory mediators. Thus, the compounds of the present invention also inhibit the production of Tumor Necrosis Factor, a serum glycoprotein, which is involved in the pathogenesis of a number of autoimmune and inflammatory diseases. TNF-α production in pro-inflammatory cells becomes attenuated by an elevation of intracellular cyclic adenosine 3'5'-monophosphate (cAMP) which in turn is regulated by PDE family of enzymes.

Nonselective PDE inhibitors like theophylline have been used for the treatment of bronchial asthma and the side effects of which include cardiac dysarhythmias and nausea which are believed to be the results of non selectivity among PDEs Of the 11 known isozymes of the PDE family, PDE4 appears to be the predominant in various inflammatory cells and hence the current research on selective PDE4 inhibitors.

First generation PDE4 inhibitors include Rolipram and Ro20-1724 which belong to the catechol diether group. Because of side effects like nausea, vomiting and increased gastric acid secretion their development as therapeutics has been halted.

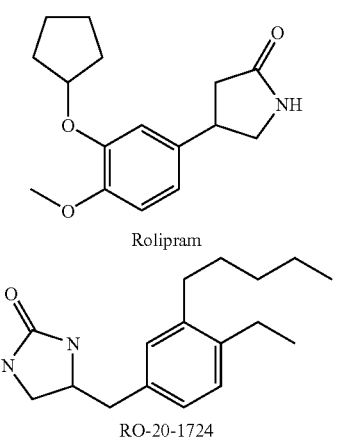

Rolipram

RO-20-1724

Current drug discovery efforts involved the design of the PDE4 inhibitors with reduced side effects while maintaining the anti inflammatory properties of rolipram. Compound like Cilomilast, roflumilast, Lirimilast and AWD-12-281 belong to the second generation PDE4 inhibitors. A few showed less side effects and roflumilast and cilomilast have progressed to the advanced stages of development.

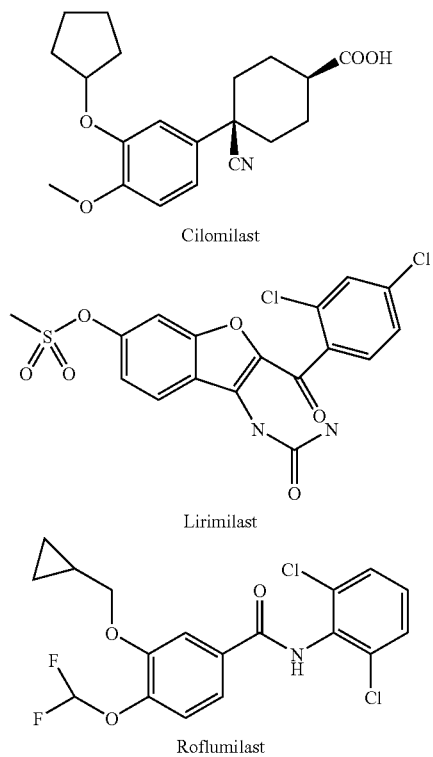

Cilomilast

Lirimilast

Roflumilast

PDE4 inhibitors can be divided into distinct classes based on structural motifs present in the molecules for e.g. Xanthine, nitraquazone, catechol diethers etc. Examples of which are theophylline, arofylline, nitraquazone, almirall, piclaminast, and filaminast, respectively. Several compounds have been developed as PDE4 inhibitors that do not fall into any one particular class of compounds like Lirimilast (BAY-19-8004), a novel sulfinate containing compound for the treatment of COPD. Tofimilast from Pfizer is an indazole derivative which is currently under clinical development. The development of ibudilast, a pyrazolopyridine compound, as a vasodilator and for the treatment of allergic ophthalmic disease is in highest phase and for multiple sclerosis it is in phase II trials. BAY-61-9987 belongs to imidazotriazinones under development by Bayer for the potential treatment of respiratory diseases (GB2388594A1-2003).

PDE4 inhibitors have been shown to relax airway smooth muscle and to suppress the activation of inflammatory cells. PDE4 inhibitors that are at various stages of clinical development are cilomilast, roflumilast, AWD-12-281,CC-10004, ONO-6126 and GRC-3886. GRC3886 inhibits PDE4 isozyme subtypes A,B,C and D. It has a good oral bioavailability across various animal species and no emetic effect had been noted at oral dosages of up to 100 mg/kg. The drug was safe, well tolerated and has excellent pharmacokinetics with a long half-life.

Patent application WO 93/19749 claims the compounds of formula I which are useful for allergy and inflammatory states.

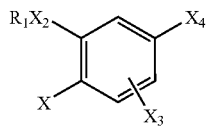

Where $X_4$ is

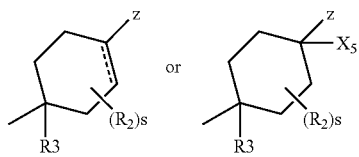

One of the representative examples of this patent is as given below.

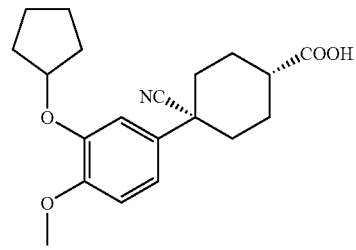

U.S. Pat. No. 5,712,298 claims the compounds of formula I which is a phosphodiesterase inhibitor for treating airway disorder and dermatitis.

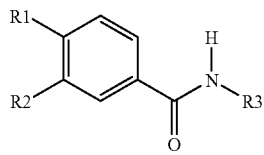

R1 is 1-4C-alkoxy which is completely or partially substituted by fluorine,

R2 is 3-5C-cycloalkylmethoxy or benzyloxy and

R3 is 2-bromophenyl, 2,6-dichloro-4-ethoxycarbonylphenyl, 2,6-dimethyoxyphenyl, 4-cyano-2-fluorophenyl, 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3-5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl, a salt thereof, and the N-oxide of a pyridine or a salt thereof.

The claimed compounds include

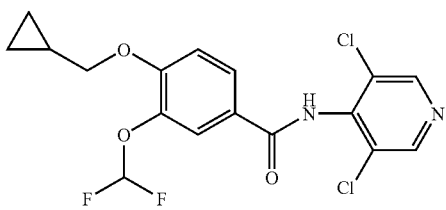

U.S. Pat. No. 5,811,455 claims the compounds of formulae I and II

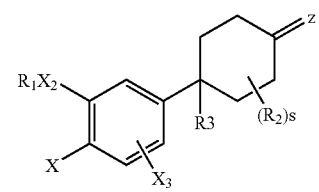

I

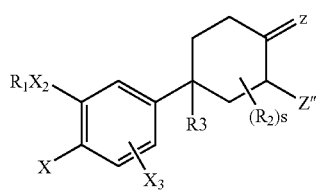

II

One of the representative examples of this invention is

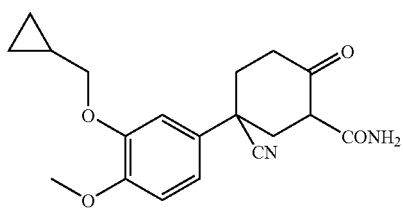

International patent application WO 2006/011024 claims the compounds of generic formula

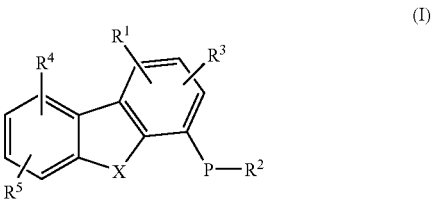

(I)

One of the representative compounds is as given below and the application claims their use in the treatment of asthma and chronic obstructive pulmonary disease apart from other disease states.

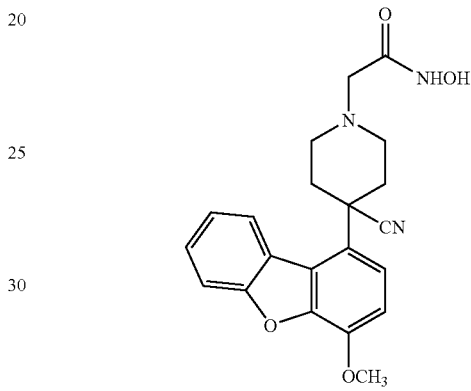

Challenges that are facing the PDE4 inhibitors are mainly nausea, vomiting, increased gastric acid secretion which may be because of selectivity towards binding sites. Based on the prior art reports compounds with selectivity for the high-affinity rolipram binding site causes side effects where as compounds with selectivity for low-affinity rolipram binding site are expected to have better therapeutic effects compared to rolipram (*J. Biol. Chem.* 1992, 267(3):1798-1804; *J. Biol. Chem.* 1999, 274(17):11796-11810). Other side effects are cardiac dysarhythmias, vasculitis and osteoporosis.

PDE10 sequences were first identified by using bioinformatics and sequence information from other PDE gene families. Homology screening of EST databases revealed PDE10A as the first member of the PDE10 family of phosphodiesterases. PDE10A has been shown by localization studies to have the most restricted distribution of all the 11 known PDE families, with the PDE10A mRNA highly expressed only in the brain and testes (*J. Biol. Chem.* (1999) 274:18438-18445; *Eur. J. Biochem* (1999)266:1118-1127). This unique distribution of PDE10A in the brain indicates a potential use of PDE10A inhibitors for treating neurological and psychiatric disorders. However, PDE10A inhibitors have also been claimed to be useful as treatment for cancer, diabetes and especially obesity.

PDE10A like all PDEs has a conserved segment of ~270 amino acids in the C-terminal end and this segment has been demonstrated to include the catalytic site. The human PDE10 gene is large, over 200 kb, with up to 24 exons coding for each of the splice variants. The amino acid sequence is characterized by two GAF domains (which bind cGMP), a catalytic region and alternatively spliced N and C termini. Numerous splice variants are possible because of at least 3 alternative exons encoding the N and 2 for the C-termini. PDE10A1, a splice variant of PDE10, is a 779 amino acid protein that hydrolyses cAMP and cGMP. The $K_m$ values for cAMP and cGMP are 0.05 and 3.0 micro molar respectively. PDE10 is a unique cAMP-inhibited cGMPase (*J. Biol. Chem.* (1999)274: 18438-18445).

PDE10A has been identified in the islets of Langerhans. PDE10A hydrolyses cAMP to AMP and thereby decreases intracellular concentrations of cAMP. By inhibiting PDE10A activity, intracellular levels of cAMP are increased thereby the release of insulin-containing secretory granules and therefore, increasing insulin secretion.

PDE10A inhibitors are known to play a role in treating cardiovascular disorders such as hypertension, ischemic heart disease, myocardial infarction and ischemic stroke. Expression of PDE10 can be detected in the heart (*Gene* 234:109-117, 1999; *Biochem. Biophy. Res. Comm,* 261:551-557, 1999), and cGMP and cAMP are important second messengers that are involved in the regulation of vascular smooth muscle tone. The PDE10 family comprises enzymes that are responsible for the degradation of cAMP and cGMP in various tissues and the activation of soluble and membrane bound guanylate cyclases leads to increased intracellular cGMP levels and induces vasodilation. The stimulation of various GPCRs (G-protein coupled receptors) which are expressed in vascular smooth muscle cells induces the activation of adenylate cyclases, generation of intracellular cAMP, and produces vasodilation. Thus PDE10A likely plays a role in the cardiovascular system.

PCT application WO 2005/012485 by Bayer claims the use of PDE10 inhibitors for the treatment of diabetes and the compounds disclosed e

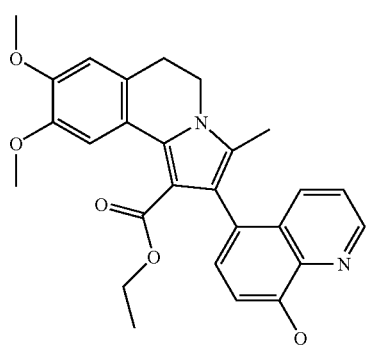

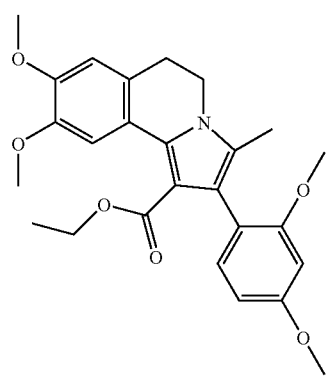

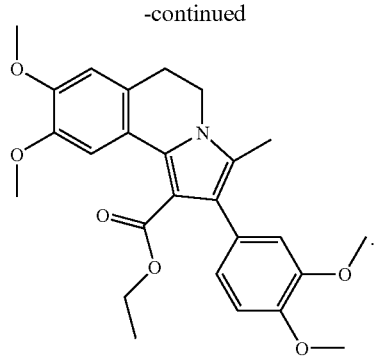

European patent application EP 1 250 923 by Pfizer broadly claims the use of selective PDE10 inhibitors for the treatment of CNS disorders exemplified by psychosis and disorders comprising deficient cognition as symptom. The only PDE10 inhibitor exemplified in this patent is papaverine and it discloses $IC_{50}$ values of papaverine for all PDE families.

PCT application WO 2004/002484 by Kyowa Hakko kogyo Co., claims the compounds of following formula as PDE10 inhibitors.

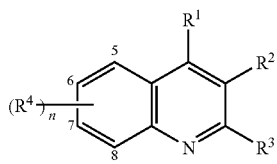

PDE10A is emerging as a particularly interest target for CNS disorders. This is due to the very restricted localization of PDE10A in key brain areas. Inhibition of PDE10A using the relatively specific PDE10A inhibitor, papaverine shows a reduction in activity and a reduced response to psychomotor stimulants. Inhibition also reduces the conditioned avoidance response predictive of clinical antipsychotic activity. PDE10 inhibitors are also shown to be potential targets in treating Diabetes and complications thereof and only a few prior art references (WO 2002/048144, WO 2003/014117, WO 2003/014116, WO 2003/014115, WO 2003/051877) by Bayer pharmaceuticals show that PDE10 inhibitors play a role in treating cancer. Due to the various roles that PDE10 inhibitors show, they have become the most promising targets for future drug therapies for different therapeutic areas.

As described above, as regulation of intracellular signaling is coordinated by PDE4, it has become a validated target for the development of therapeutics for inflammatory diseases such as asthma and COPD. PDE4 also has shown to be a potential target for CNS related diseases, depression, memory enhancement, cardiovascular disease and osteogenesis.

SUMMARY OF THE INVENTION

The present invention relates to novel phosphodiesterase inhibitors, in particular phosphodiesterase type 4 (PDE-4) and phosphodiesterase type 10 (PDE-10) inhibitors of general formula (I)

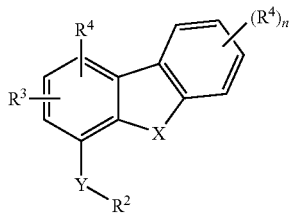

(I)

and analogs thereof, derivatives, tautomers, stereoisomers, enantiomers, diastereomers, polymorphs, pharmaceutically acceptable salts, pharmaceutically acceptable hydrates, pharmaceutically acceptable solvates, N-oxides and bioisosteres. Additionally, the present invention relates to pharmaceutical compositions containing these compounds.

Whereby in formula (I)

X represents O, S or $NR^5$ and Y represents O or S;

$R^1$ is

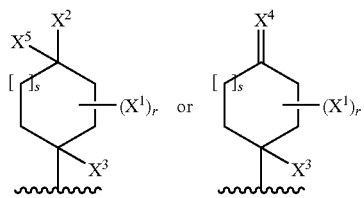

$X^1$ is selected from hydrogen, optionally substituted alkyl, optionally substituted N,N-dimethylaminoalkenyl, carboxy, =CH—$NR^5R^6$, $COOR^6$;

$X^2$ is selected from optionally halo, cyano, carboxy, $COOR^6$, substituted alkyl, $NR^5R^6$, —$NR^5S(O)_mR^6$;

$X^3$ is selected from cyano, carboxy, alkyl, amido or tetrazolyl;

$X^4$ represents O, S, $NR^5$, N—$OR^5$, =N—$OCH_2COOH$, =N—O-Me;

$X^5$ represents hydrogen, halo, hydroxyl, cyano or alkyl; or

When two $X^1$ groups are ortho to each other, they may together form a 4 to 7 membered ring system selected from alicyclic or heterocyclic ring which may be saturated, partially saturated or unsaturated, aryl, or heteroaryl. The heterocyclic or heteroaryl may have one or more heteroatoms selected from O, $NR^5$ or S; or When $X^1$ and $X^2$ are ortho to each other, they may together form a 4 to 7 membered ring system selected from alicyclic or heterocyclic ring which may be saturated, partially saturated or unsaturated, aryl or heteroaryl having one or more heteroatoms selected from O, $NR^5$ or S. The 4 to 7 membered ring system may optionally be mono- or di-substituted with oxo (=O), carboxy, R'COOR6, R'$NR^5R^6$, $OR^5$, alkyl or aryl. Representative examples of the 4 to 7 membered rings with optional substitutions include but not limited to

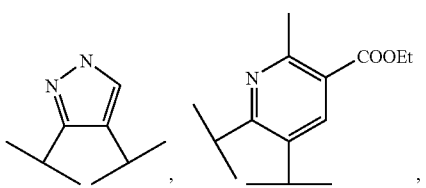

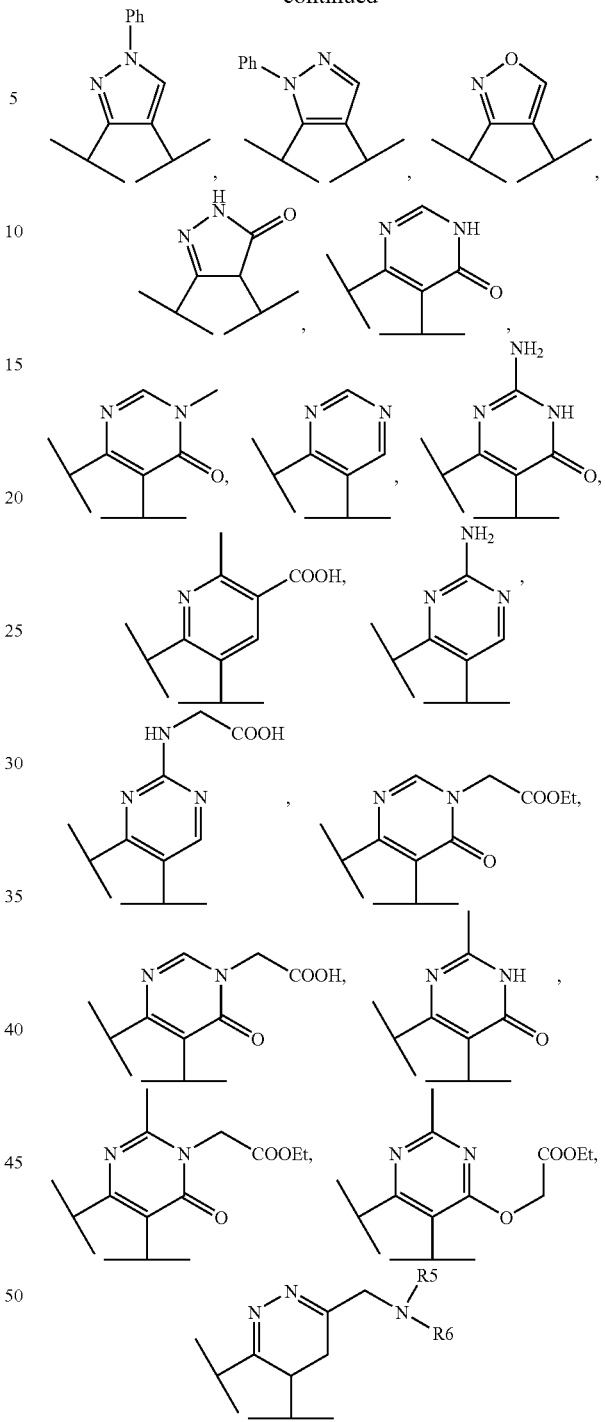

r is an integer represented by 0, 1, 2 or 3;

s is an integer represented by 0, 1 or 2;

$R^2$ represents optionally substituted groups selected from alkyl, haloalkyl, alkenyl, alkynyl, optionally substituted cycloalkyl, optionally substituted aryl, optionally substituted heteroaryl or optionally substituted heterocyclyl;

$R^3$ and $R^4$ independently represent hydrogen, hydroxy, halo, cyano, amino, alkyl, alkoxy, alkenyl, alkynyl, alkylamino, formyl, carboxy or carbamoyl;

$R^5$ represents hydrogen, alkoxy, R'$COOR^6$, optionally substituted alkyl or optionally substituted aryl;

$R^6$ represents hydrogen, optionally substituted alkyl or optionally substituted aryl; or $R^5$ and $R^6$ together may form a 3 to 12 membered mono or polycyclic ring which may be saturated, partially saturated or unsaturated and may optionally contain one more heteroatom selected form O, N, S, and may optionally be mono- or di-substituted;

R' represents a direct bond or an optionally substituted alkylene;

n is an integer represented by 0, 1, 2 or 3;

m is an integer represented by 0, 1 or 2;

In another aspect of the present invention, when two $R^4$ groups are ortho to each other, they may join together to form a saturated, unsaturated or partially saturated ring which may optionally include upto 2 heteroatoms selected from O, S and $NR^5$ In another aspect of the present invention, when X is $NR^5$, then $R^2$ and $R^5$ may join together to form a saturated or unsaturated 5 to 7 membered ring which may optionally contain one or two additional heteroatoms and may be optionally substituted;

In yet another aspect, the present invention relates to a process for the preparation of the novel heterocyclic compounds of general formula (I).

In yet another aspect, the present invention relates to the pharmaceutical compositions using compounds of general formula (I).

The compounds of the present invention inhibit or regulate the TNF alpha production and are useful in the treatment of allergic and inflammatory diseases including asthma, inflammatory diseases, allergic conditions, allergic conjunctivitis, eosinophilic granuloma, psoriasis, rheumatoid arthritis, diabetes, crohn's disease allergic rhinitis endotoxic shock and adult respiratory distress syndrome. The compounds of present invention are particularly useful for the treatment of asthma and chronic obstructive pulmonary disease (COPD).

DETAILED DESCRIPTION OF THE INVENTION

The term "alkyl" refers to a straight or branched chain saturated aliphatic hydrocarbon that may be optionally substituted with multiple degrees of substitution being allowed. Examples of "alkyl" include but are not limited to methyl, ethyl, n-propyl, isopropyl, n-butyl, t-butyl, n-pentyl, isobutyl and the like and the substitutions may be selected from halogens, hydroxy, alkoxy, acyl, amino, nitro and like. Unless specified by for example, the phrase "$C_x$-$C_y$ alkyl" which refers to an alkyl group with specified number of carbons, in the entire specification the term "alkyl group" refers to $C_1$-$C_6$ and a similar terminology will apply for other preferred ranges as well.

The term "alkenyl" used herein, either alone or in combination with other radicals, denotes a straight or branched $C_2$-$C_6$ aliphatic hydrocarbon chain containing one or more carbon to carbon double bonds that may be optionally substituted with multiple degrees of substitution being allowed. The term "alkenyl" includes dienes and trienes of straight and branched chains and are selected form vinyl allyl, 2-butenyl, 3-butenyl, 2-pentenyl, 3-pentenyl, 4-pentenyl, 2-hexenyl, 3hexenyl, 4-hexenyl, 5-hexenyl, 2-heptenyl, 3-heptenyl, 4-heptenyl, 5-heptenyl, 6-heptenyl The term "alkynyl" used herein, either alone or in combination with other radicals, denotes a, straight or branched chain aliphatic hydrocarbon containing two to eight carbons with one or more triple bonds which may be optionally substituted with multiple degrees of substitution being allowed. The term "alkynyl" includes di- and tri-ynes, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 4-hexynyl, 5-hexynyl, and the like.

The term "alkylene", refers to a divalent alkyl linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

The term "alkoxy" refers to a group —Oalkyl where alkyl is as herein defined. Representative examples include but are not limited to methoxy, ethoxy and the like The term "haloalkyl" refers to the group '$R_c$-halogen' where $R_c$ is alkyl defined as above and halogen is selected from fluorine, chlorine, bromine and Iodine and it can be haloalkyl, dihaloalkyl or trihaloalkyl or polyhaloalkyl like methylene chloride, $CF_3$, $CHF_2$, $CF_2$—$CF_3$ etc.

The term "halo" refers to fluorine, chlorine, bromine or iodine;

The term "aryl" refers to a $C_5$-$C_{12}$ aromatic ring system which may be monocyclic, bicyclic or polycyclic. The term includes ring(s) optionally substituted with multiple degrees of substitution being allowed and the substitutions may include halogens, nitro, amino, alkoxy, alkyl sulfonyl amino, alkylcarbonylamino, carboxy, alkyl carbonoyl, hydroxy, and alkyl. Exemplary aryl groups include phenyl, naphthyl, indanyl, biphenyl and the like.

The term "cycloalkyl" used herein, either alone or in combination with other radicals, denotes a mono, bicyclic or polycyclic saturated, partially saturated hydrocarbon ring system of about 3 to 12 carbon atom which may be optionally substituted with halogens, nitro, amino, alkoxy, alkyl sulfonyl amino, alkylcarbonylamino, carboxy, alkyl carbonoyl, hydroxy, and alkyl. Exemplary "cycloalkyl" groups include but are not limited to cyclopopyl, cyclobutyl, cyclopentyl, cyclohexyl and cycloheptyl, perhydronapthyl, adamantyl, noradamantyl or spirobicyclic groups such as spiro(4,4)non-2-yl.

The term "heteroaryl" refers to monocyclic aromatic ring system or a fused polycyclic aromatic ring systems comprising two or more aromatic rings preferably two to three ring systems. These heteroaryl rings contain one or more nitrogen, sulfur and or oxygen atoms where N-oxides, sulfur oxides and dioxides are permissible heteroatom substitutions. The term includes rings optionally substituted with halogens, nitro, amino, alkoxy, alkyl sulfonyl amino, alkylcarbonylamino, carboxy, alkyl carbonoyl, hydroxy, and alkyl. Examples of heteroaryl groups include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, chromanyl, isochromanyl and the like.

The term "heterocyclyl" refers to a stable 3 to 15 membered ring that is either saturated, has one or more degrees of unsaturation or is unsaturated. These heterocyclic rings contain one or more heteroatoms selected from the group consisting of nitrogen, sulfur and/or oxygen atoms where N-oxides, sulfur oxides and dioxides are permissible heteroatom substitutions. Such a ring may be optionally fused to one or more of another heterocyclic ring(s), aryl ring(s) or cycloalkyl ring(s). Examples of such groups may be selected from the group comprising azetidinyl, acridinyl, pyrazolyl, imidazolyl, triazolyl, pyrrolyl, thiophenyl, thiazolyl, oxazolyl, isoxazolyl, furanyl, pyrazinyl, tetrahydroisoquinolyl, piperidinyl, piperazinyl, morpholinyl, thiomorphonilyl, pyridazinyl, indolyl, isoindolyl, quinolyl, chromanyl and the like.

The term "carbamoyl" refers to the group —C(O)NH2.

The term "carboxy" refers to —COOH.

The term "stereoisomers" refers to certain compounds described herein that contain one or more chiral centres or may otherwise be capable of existing as multiple stereoisomers. Scope of the present invention includes pure stereoisomers as well as mixtures of stereoisomers such as purified enantiomers/diastereomers or enantiomerically/diastereomerically enriched mixtures.

The term "bioisosteres" refers to compounds or groups that possess near molecular shapes and volumes, approximately the same distribution of electrons and which exhibit similar physical properties such as hydrophobicity. Bioisostereic compounds affect the same biochemically associated systems as agonist or antagonists and thereby produce biological properties that are related to each other.

The term "pharmaceutically acceptable salts" forming part of this invention include salts derived from inorganic bases such as Li, Na, K, Ca, Mg, Fe, Cu, Zn, Al, Mn; salts of organic bases such as N,N'-diacetylethylenediamine, 2-dimethylaminoethanol, isopropylamine, morpholine, piperazine, piperidine, procaine, diethylamine, triethylamine, trimethylamine, tripropylamine, tromethamine, adamentyl amine, diethanolamine, ethylenediamine, N,N-benzyl phenylethylamine, choline hydroxide, dicyclohexylamine, metformin, benzylamine, phenylethylamine, dialkylamine, trialkylamine, thiamine, aminopyrimidine, aminopyridine, purine, pyrimidine, spermidine, and the like; chiral bases like alkylphenylamine, glycinol, phenyl glycinol and the like, salts of natural amino acids such as glycine, alanine, valine, leucine, isoleucine, norleucine, tyrosine, cystine, cystine, methionine, proline, hydroxy proline, histidine, ornithine, lysine, arginine, serine, threonine, phenylalanine; unnatural amino acids such as D-isomers or substituted amino acids; salts of acidic amino acids such as aspartic acid, glutamic acid; guanidine, substituted guanidine wherein the substituents are selected from nitro, amino, alkyl, alkenyl, alkynyl, ammonium or substituted ammonium salts. Where appropriate, the salts may include acid addition salts which are sulphates, nitrates, phosphates, perchlorates, borates, hydrohalides, acetates, tartrates, maleates, citrates, succinates, palmoates, methanesulfonates, benzoates, salicylates, hydroxynaphthoates, benzenesulfonates, ascorbates, glycerophosphates, ketoglutarates and the like.

The term "pharmaceutically acceptable solvates" may be hydrates or comprising other solvents of crystallization such as alcohols.

The term "suitable pharmaceutically acceptable carriers" includes solid fillers or diluents and sterile aqueous or organic solutions. The active ingredient will be present in such pharmaceutical compositions in the amounts sufficient to provide the desired dosage in the range as described above. Thus, for oral administration, the compounds can be combined with a suitable solid, liquid carrier or diluent to form capsules, tablets, powders, syrups, solutions, suspensions and the like. The pharmaceutical compositions, may, if desired, contain additional components such as flavourants, sweeteners, excipients and the like.

The term "compounds of the invention" or "present invention" refers to the compounds of the present invention represented by formula (I) as herein defined, its derivatives, analogs, tautomeric forms, stereoisomers, bioisosters, diastereomers, polymorphs, enantiomers, appropriate N-oxides, pharmaceutically acceptable salts, pharmaceutically acceptable hydrates, pharmaceutically acceptable solvates and pharmaceutically acceptable compositions containing them.

The present invention relates to novel phosphodiesterase inhibitors, in particular phosphodiesterase type 4 (PDE-4) and phosphodiesterase type 10 (PDE-10) inhibitors of general formula (I)

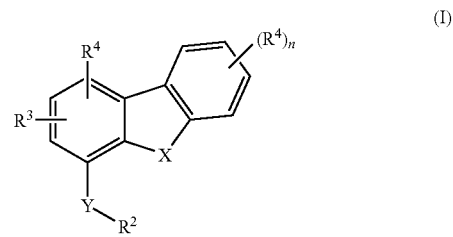

(I)

and analogs thereof, derivatives, tautomers, stereoisomers, enantiomers, diastereomers, polymorphs, pharmaceutically acceptable salts, pharmaceutically acceptable hydrates, pharmaceutically acceptable solvates, N-oxides and bioisosteres. Additionally, the present invention relates to pharmaceutical compositions containing these compounds.

Whereby in formula (I)

X represents O, S or $NR^5$ and Y represents O or S;

$R^1$ is

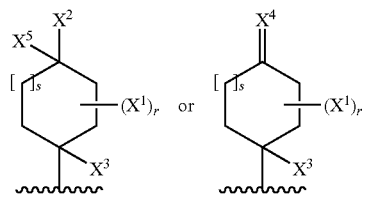

$X^1$ is selected from hydrogen, optionally substituted alkyl, optionally substituted N,N-dimethylaminoalkenyl, carboxy, =CH—$NR^5R^6$, and $COOR^6$;

$X^2$ is selected from optionally halo, cyano, carboxy, $COOR^6$, substituted alkyl, $NR^5R^6$, —$NR^5S(O)_mR^6$;

$X^3$ is selected from cyano, carboxy, alkyl, amido or tetrazolyl;

$X^4$ represents O, S, $NR^5$, N—$OR^5$, =N—$OCH_2COOH$, =N—O-Me;

$X^5$ represents hydrogen, halo, hydroxyl, cyano or alkyl; or

When two $X^1$ groups are ortho to each other, they may together form a 4 to 7 membered ring system selected from alicyclic or heterocyclic ring which may be saturated, partially saturated or unsaturated, aryl, or heteroaryl. The heterocyclic or heteroaryl may have one or more heteroatoms selected from O, NR5 or S; or When $X^1$ and $X^2$ are ortho to each other, they may together form a 4 to 7 membered ring system selected from alicyclic or heterocyclic ring which may be saturated, partially saturated or unsaturated, aryl or heteroaryl having one or more heteroatoms selected from O, $NR^5$ or S. The 4 to 7 membered ring system may optionally be mono or di-substituted with oxo (=O), carboxy, R'COOR6, R'$NR^5R^6$, $OR^3$, alkyl, aryl. Representative examples of the 4 to 7 membered rings with optional substitutions include but not limited to

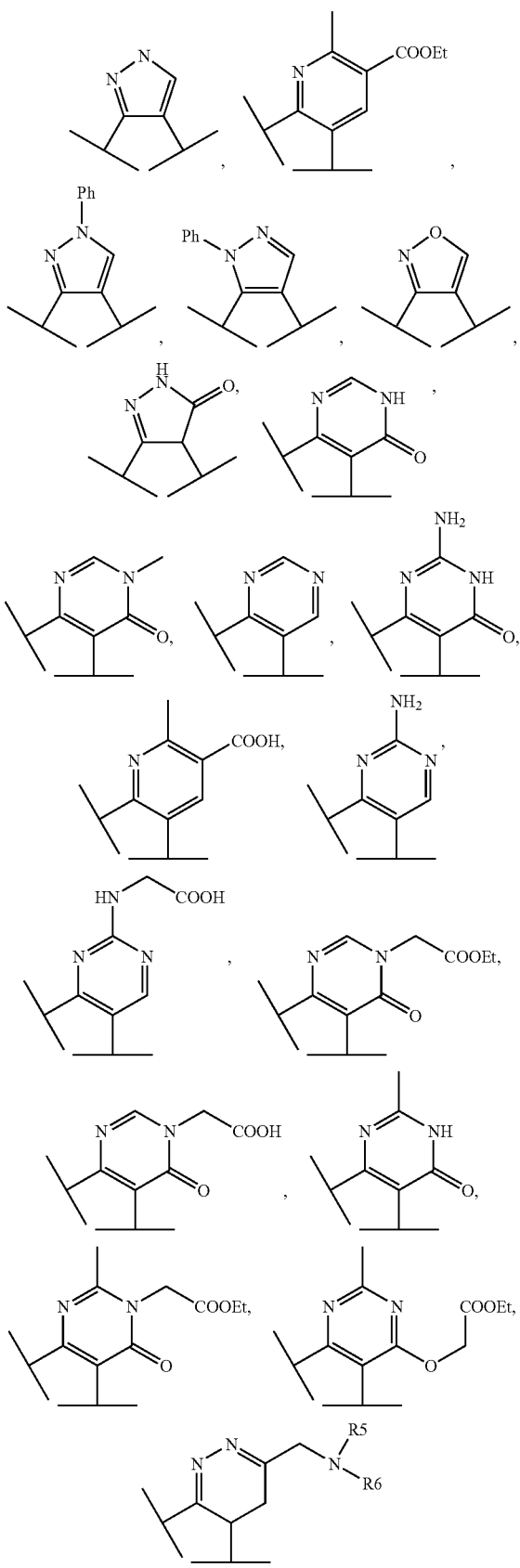

r is an integer represented by 0, 1, 2 or 3;

s is an integer represented by 0, 1 or 2;

R² represents optionally substituted groups selected from alkyl, haloalkyl, alkenyl, alkynyl, optionally substituted cycloalkyl, optionally substituted aryl, optionally substituted heteroaryl or optionally substituted heterocyclyl;

R³ and R⁴ independently represent hydrogen, hydroxy, halo, cyano, amino, alkyl, alkoxy, alkenyl, alkynyl, alkylamino, formyl, carboxy, carbamoyl; or when two R⁴ groups are ortho to each other, they may join together to form a saturated, unsaturated or partially saturated ring which may optionally include up to 2 heteroatoms selected from O, S and NR⁵;

R⁵ represents hydrogen, alkoxy, R'COOR⁶, optionally substituted alkyl or optionally substituted aryl;

R⁶ represents hydrogen, optionally substituted alkyl or optionally substituted aryl; or R⁵ and R⁶ together form a 3 to 12 membered mono or polycyclic ring which may be saturated, partially saturated or unsaturated and may optionally contain one more heteroatom selected form O, N, S, and may optionally be mono or di-substituted;

R' represents a direct bond or an optionally substituted alkylene;

n is an integer represented by 0, 1, 2, or 3;

m is an integer represented by 0, 1 or 2; or when X is NR⁵, then R² and R⁵ may join together to form a saturated or unsaturated 5 to 7 membered ring which may optionally contain one or two additional heteroatoms and may be optionally substituted.

Preferred is a compound of general formula (I) wherein X is S;

Further preferred is where X is O;

Further preferred is where X is NR⁵, wherein R⁵ is hydrogen, optionally substituted alkyl or optionally substituted aryl;

Further preferred is where R⁵ is hydrogen;

Further preferred is where R⁵ is optionally substituted groups selected from methyl, ethyl, propyl;

Further preferred is where Y is S;

Further preferred is where Y is O;

Further preferred is where X¹ is carboxy;

Further preferred is where X¹ is COOR⁶ wherein R⁶ is alkyl preferably methyl or ethyl;

Further preferred is where X¹ is N,N-dimethylaminoalkenyl;

Further preferred is where X² is carboxy;

Further preferred is where X² is COOR⁶ wherein R⁶ is alkyl preferably methyl or ethyl;

Further preferred is where X² is NR⁵S(O)$_m$R⁶, wherein R⁵ is hydrogen, m is integer 2 and R⁶ is methyl;

Further preferred is where X¹ and X² when ortho to each other, forms a 4 to 7 membered ring system selected from alicyclic or heterocyclic ring which may be saturated, partially saturated or unsaturated, aryl or heteroaryl having one or more heteroatoms selected from O, NR⁵ or S. The 4 to 7 membered ring system may optionally be mono or di-substituted with Oxo (=O), carboxy, R'COOR⁶, R'NR⁵R⁶, OR⁵, alkyl, aryl;

Further preferred is where X³ is cyano;

Further preferred is where X⁴ is O;

Further preferred is where $X^4$ is S;

Further preferred is where $X^4$ is N—$OR^5$ wherein $R^5$ is alkoxy preferably methoxy; Further preferred is where $X^4$ is =N—$OCH_2COOH$;

Further preferred is where $X^5$ is hydrogen;

Further preferred is where $R^2$ is alkyl preferably methyl or ethyl;

Further preferred is where $R^3$ is hydrogen;

Further preferred is where $R^4$ is hydrogen;

Further preferred is where when X is $NR^5$, then $R^2$ and $R^5$ may join together to form a saturated or unsaturated 5 to 7 membered ring which may optionally contain one or two additional heteroatoms and can be optionally substituted In yet another aspect the present invention also relates to a process for the preparation of the novel heterocyclic compounds of general formula (I).

In yet another aspect the present invention also relates to the pharmaceutical compositions using compounds of general formula (I).

Representative compounds of the present invention listed below are illustrative in nature only and do not limit to the scope of the invention.

1. Methyl 5-cyano-5-(4-methoxydibenzo[b,d]furan-1-yl)-2-oxocyclohexane carboxylate
2. 1-(4-Methoxydibenzo[b,d]furan-1-yl)-4-oxocyclohexanecarbonitrile
3. 4-Cyano-4-(4-methoxydibenzo[b,d]furan-1-yl)cyclohexanecarboxylic acid
4. 5-(4-Methoxydibenzo[b,d]furan-1-yl)-4,5,6,7-tetrahydro-2H-indazole-5-carbonitrile
5. N-[4-Cyano-4-(4-methoxydibenzo[b,d]furan-1-yl)cyclohexyl]methanesulfonamide
6. (3E)-3-[(Dimethylamino)methylene]-1-(4-methoxydibenzo[b,d]furan-1-yl)-4-oxocyclohexanecarbonitrile
7. Ethyl 6-cyano-6-(4-methoxydibenzo[b,d]furan-1-yl)-2-methyl-5,6,7,8-tetrahydro quinoline-3-carboxylate
8. 5-(4-Methoxydibenzo[b,d]furan-1-yl)-1-phenyl-4,5,6,7-tetrahydro-1H-indazole-5-carbonitrile
9. 5-(4-Methoxydibenzo[b,d]furan-1-yl)-2-phenyl-4,5,6,7-tetrahydro-2H-indazole-5-carbonitrile
10. 6-Cyano-6-(4-methoxydibenzo[b,d]furan-1-yl)-2-methyl-5,6,7,8-tetrahydro quinoline-3-carboxylic acid
11. 5-(4Ethoxydibenzo[b,d]furan-1-yl)-4,5,6,7-tetrahydro-2,1-benzisoxazole-5-carbonitrile
12. 5-(4-Methoxydibenzo[b,d]furan-1-yl)-3-oxo-3,3a,4,5,6,7-hexahydro-2H-indazole-5-carbonitrile
13. 6-(4-Methoxydibenzo[b,d]furan-1-yl)-4-oxo-3,4,5,6,7,8-hexahydroquinazoline-6-carbonitrile
14. 6-(4-Methoxydibenzo[b,d]furan-1-yl)-3-methyl-4-oxo-3,4,5,6,7,8-hexahydroquinazoline-6-carbonitrile
15. 6-(4-Methoxydibenzo[b,d]furan-1-yl)-5,6,7,8-tetrahydroquinazoline-6-carbonitrile
16. 2-Amino-6-(4-methoxydibenzo[b,d]furan-1-yl)-4-oxo-3,4,5,6,7,8-hexahydroquinazoline-6-carbonitrile
17. 2-Amino-6-(4-methoxydibenzo[b,d]furan-1-yl)-5,6,7,8-tetrahydroquinazoline-6-carbonitrile
18. {[6-Cyano-6-(4-methoxydibenzo[b,d]furan-1-yl)-5,6,7,8-tetrahydroquinazolin-2-yl]amino}acetic acid
19. Ethyl[6-cyano-6-(4-methoxydibenzo[b,d]furan-1-yl)-4-oxo-5,6,7,8-tetrahydroquinazolin-3(4H)-yl]acetate
20. [6-Cyano-6-(4-methoxydibenzo[b,d]furan-1-yl)-4-oxo-5,6,7,8-tetrahydroquinazolin-3(4H)-yl]acetic acid
21. 6-(4-Methoxydibenzo[b,d]furan-1-yl)-2-methyl-4-oxo-3,4,5,6,7,8-hexahydroquinazoline-6-carbonitrile
22. Ethyl[6-cyano-6-(4-methoxydibenzo[b,d]furan-1-yl)-2-methyl-4-oxo-5,6,7,8-tetrahydroquinazolin-3(4H)-yl]acetate
23. Ethyl{[6-cyano-6-(4-methoxydibenzo[b,d]furan-1-yl)-2-methyl-5,6,7,8-tetrahydroquinazolin-4-yl]oxy}acetate
24. 1-(4-Methoxydibenzo[b,d]furan-1-yl)-4-(methoxyimino)cyclohexanecarbonitrile
25. ({[4-Cyano-4-(4-methoxydibenzo[b,d]furan-1-yl)cyclohexylidene]amino}oxy)acetic acid or a pharmaceutically acceptable salt thereof.

Another embodiment of the present invention is a method of treating an inflammatory disease, disorder or condition associated with undesirable inflammatory immune response or a disease or condition induced by or associated with an excessive secretion of TNF-α and Phosphodiesterase 4 (PDE IV) in humans. The method includes administering to the human a therapeutically effective amount of a compound according to the general formula I. "Method of treating" includes preventing or delaying the appearance of clinical symptoms, inhibiting the state disorder or condition, relieving the disease causing regression of the disease.

Preferred inflammatory conditions and immune disorders are chosen from the group comprising of asthma, COPD, allergic rhinitis, allergic conjunctivitis, respiratory distress syndrome, chronic bronchitis, nephritis, rheumatoid spondylitis, osteoarthritis, atopic dermatitis, eosinophilic granuloma, psoriasis, rheumatoid septic shock, ulcerative colitis, parkinson's disease; multiple sclerosis, chronic inflammation, crohn's syndrome also other inflammatory conditions of lungs, eyes, joints, bowels, skin and heart central nervous system (CNS). Preferred diseases of CNS are depression, amnesia, dementia, alzheimer's disease, cardiac failure, shock and cerebrovascular disease.

Scheme 1

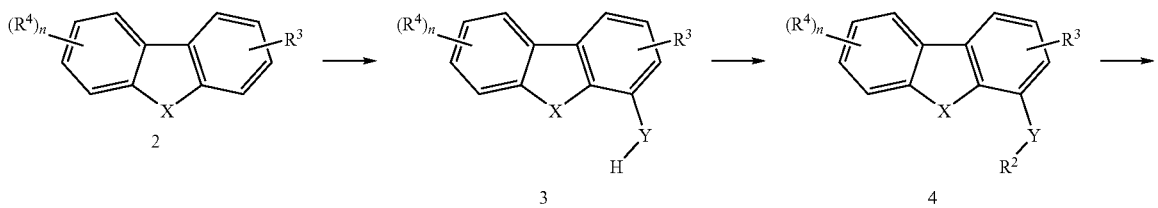

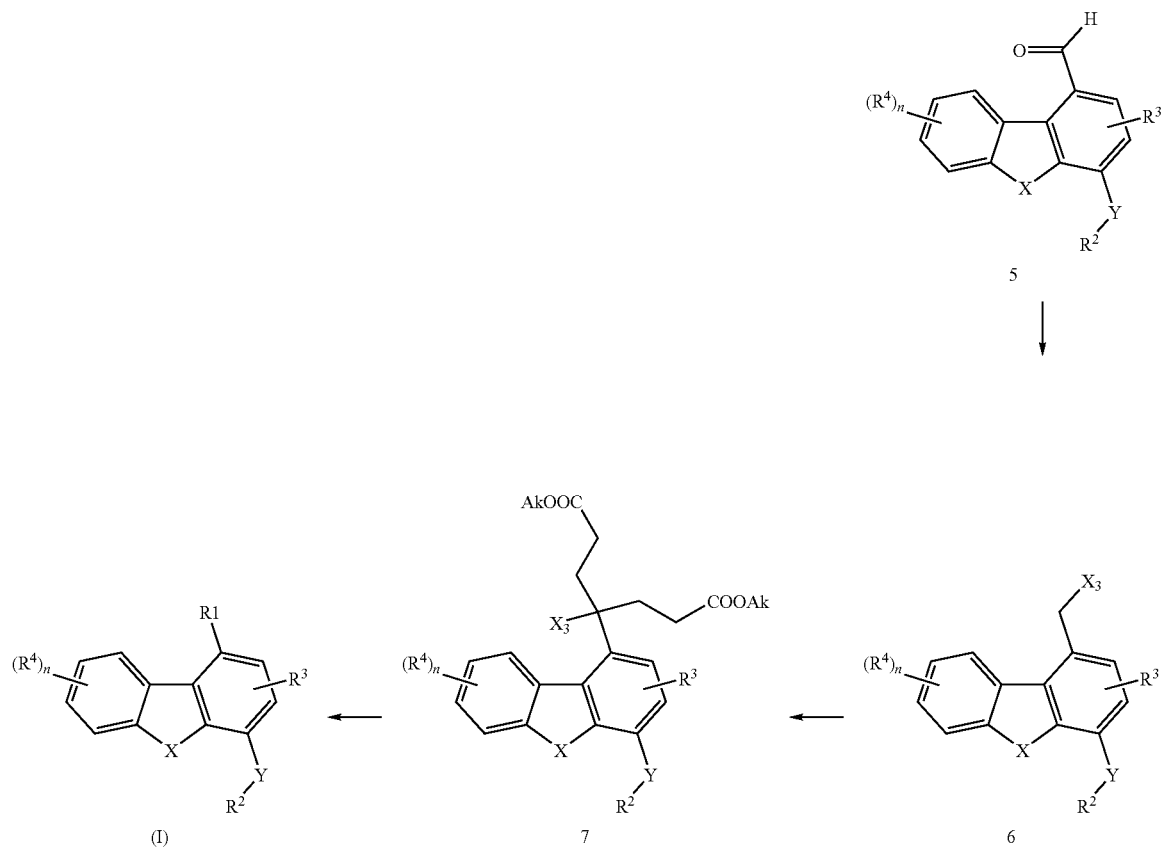

In the above mentioned scheme, the compound of formula 2 is synthesized from commercially available compounds like dibenzofuran or carbazole. Compound of general formula 3 is prepared from compound of formula 2 under basic conditions using bases such as BuLi in the presence of an oxygen source like oxygen or hydrogen peroxide etc. The compound of formula 3 can be alkylated to compound of formula 4 (where $R^2$ is alkyl) using an alkylating agent such as alkyl halide under basic conditions. Basic conditions can be achieved by sodium or potassium salts or sodium hydride in aprotic polar solvents like DMSO, dimethyl formamide, dimethylacetamide or n-methylpyrrolidone. Compounds of formula 5 can be prepared from compounds of formula 4 by carrying out a formylation using dichloromethyl methyl ether in the presence of lewis catalysts like $AlCl_3$, $TiCl_4$, $SnCl_4$, $FeCl_3$, $ZnCl_2$. Compounds of formula 6 can be obtained from compounds of formula 5 by reduction of the aldehyde and chlorination followed by cyanation using any conventional cyanation processes like with sodium cyanide etc. Further reaction of the cyano compound with alkylacrylate in presence of triton B gives the compound of formula 7. The intra molecular cyclisation of the diester of formula 7 in the presence of a base like sodium hydride in dimethoxymethane followed by deesterification in the presence of sodium chloride in DMSO-water gives the compound of formula (I).

21
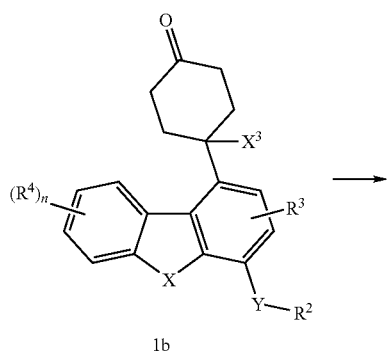
1b
22
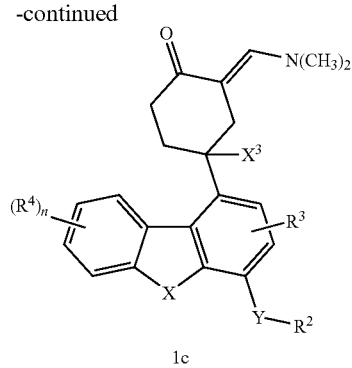
1c
Compounds of formula 1a can be converted into compounds of formula 1b according to scheme 1 and compounds of formula 1c are obtainable by condensation of 1b with dimethyl formamide dimethyl acetal in presence of a base such as triethylamine or tetraethylamine.
Scheme 3
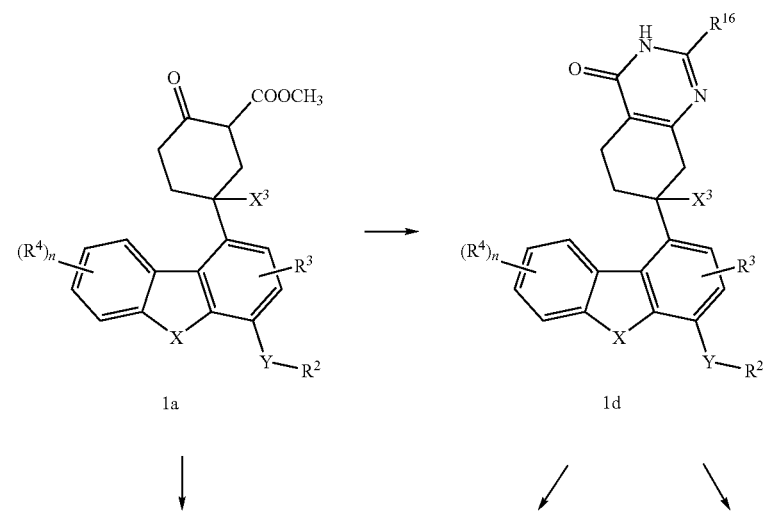
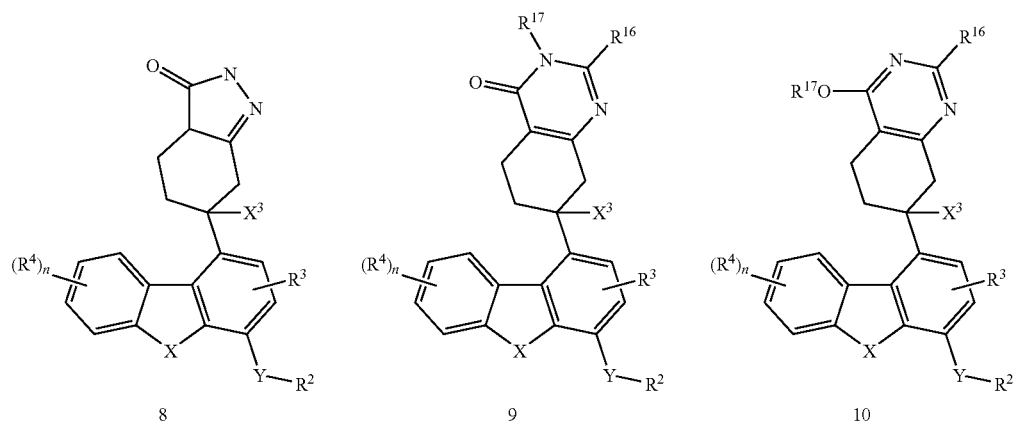

Condensation of formula 1a with nucleophiles of general formula NH=C(NH$_2$)—R$^{16}$ gives the intermediate compound of formula 1d which upon alkylation in the presence of alkali metal carbonates like cesium carbonate gives N-alkylated and O-alkylated compounds 9 and 10. Selectivity is generally based on the group present at X$^3$. Also, compounds of formula 1a when condensed with hydrazine in alkanols like methanol or IPA at temperatures of about 25° C. to 100° C. form compound of formula 8 wherein X, R$^2$, R$^3$, R$^4$, R$^{16}$, R$^{17}$, X$^3$, n are as described above Compounds of formula 13 can be obtained from compounds of formula (I) by following the steps comprising reacting the cyclohexanone compound with a tosyloxy compound and further reacting the tosyl-compound with amidines in the presence of a base. Compounds of formula 14 can be obtained from compounds of formula 1b by following the steps comprising reacting the cyclohexanone compound with amino aldehydes, where the amino group is protected, in the presence of a base and cyclising the compound to the desired indole derivative under suitable acidic conditions. It

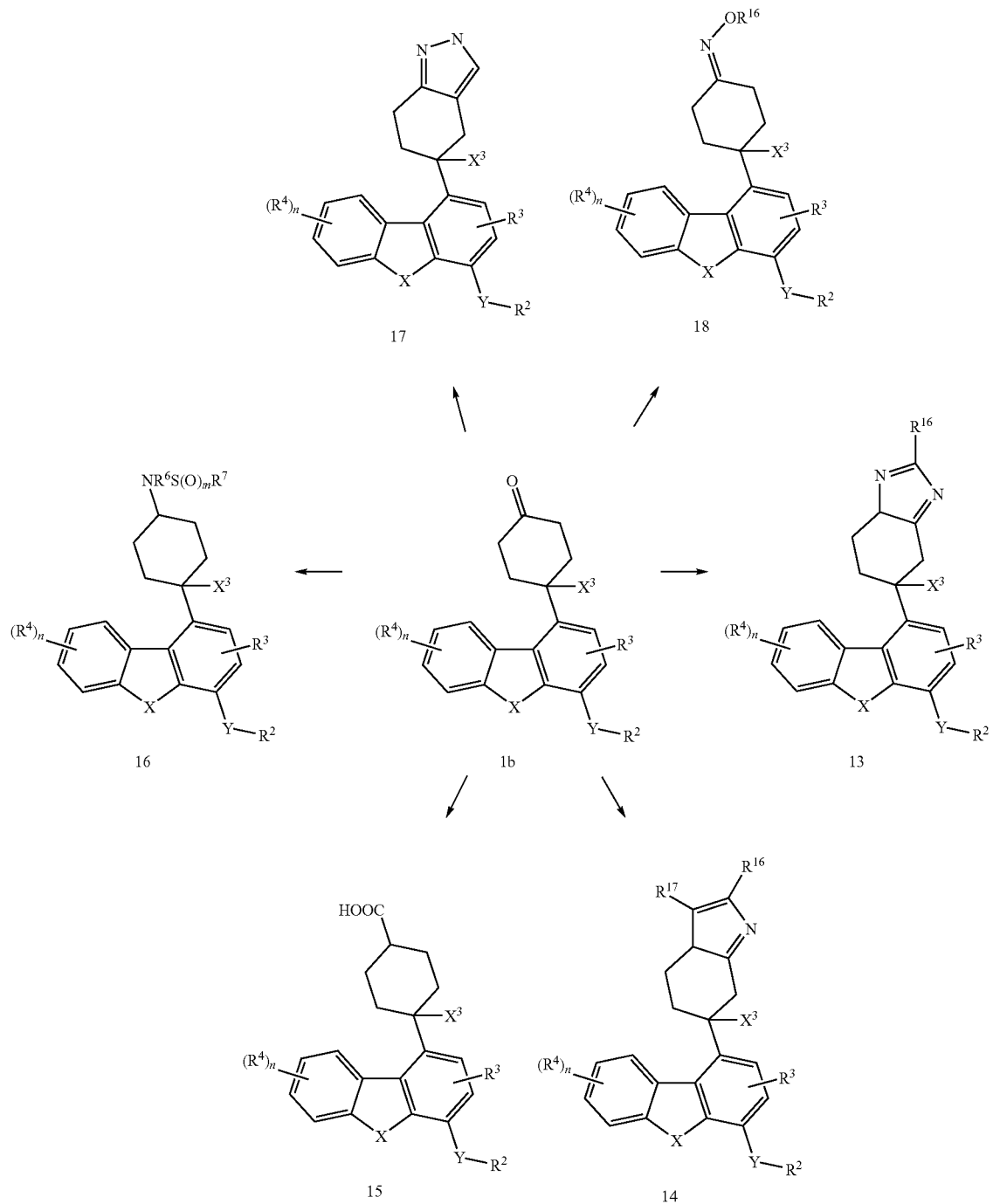

Scheme 4 can further be functionalized to give an optionally substituted indole derivative of formula 14. Compounds of formula 15 can be obtained by following the steps comprising keto-protection of formula 1b and esterification followed by hydrolysis of the epoxide ester to yield the acid and further removal of epoxide in the presence of an inorganic salt and an aprotic solvent like DMSO. Compounds of formula 16 can be obtained from compounds of formula 1b by following the steps comprising reacting the cyclohexanone compound with an amine followed by reacting with alkylsulfonyl halides in the presence of a mild base like triethylamine and in the presence of solvents like dichloromethane. Compounds of formula 17 can be obtained from compounds of formula 1b by formylating cyclohexanone of formula 1b and reacting the product with hydroxylamine or it's salts in the presence of an alkali base at ambient temperatures. Compounds of formula 18 can be obtained from compounds of formula 1b by reacting the cyclohexanone compound with an oxime or substituted oximes in the presence of an alcohol as solvent.

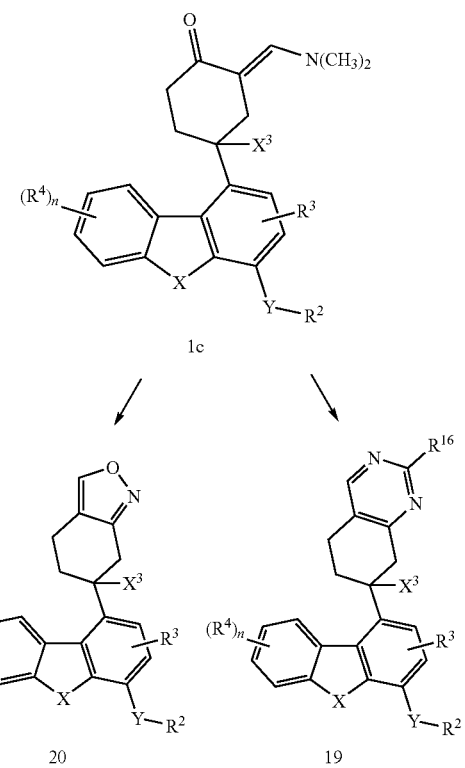

Compound of formula 1c can be converted into compounds of formula 19 by reacting them with amidines in the presence of suitable organic or inorganic bases such as alkali bases like KOH, bicarbonates like $NaHCO_3$ or organic bases like triethylamine and pyridine. Compounds of formula 20 can be obtained from compounds of formula 1c by reaction with hydroxylamine or its salts under basic conditions in the presence of alcohols. Compounds of formula 1c on reaction with an ester in the presence of ammonium acetate and acetic acid forms an intermediate compound which on further hydrolysis under basic conditions gives the compounds of formula 21. Compounds of formula 1c on reaction with hydrazines or substituted hydrazines of formula $R^{17}HN-NHR^{16}$ in an alcoholic solvent at a temperature of about 20° C. to about 60° C. give compounds of formula 22.

Scheme 5

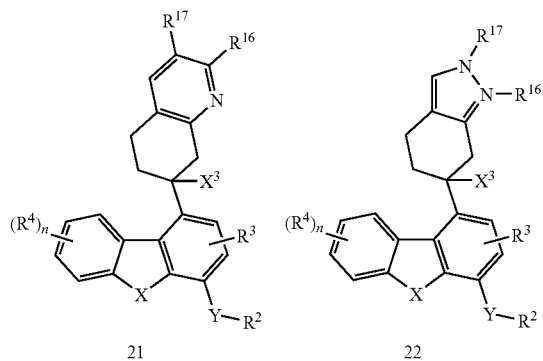

Scheme 6

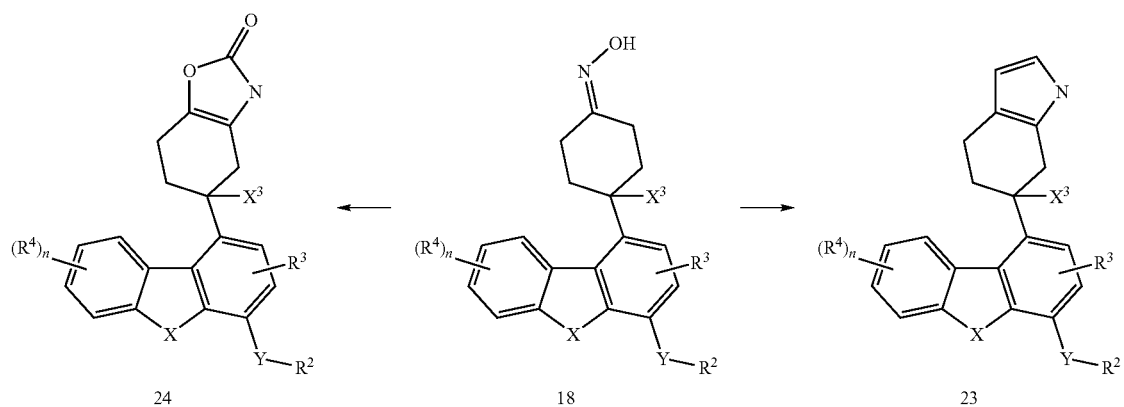

Compounds of formula 23 can be obtained from compounds of formula 18 by the reaction with acetylene gas in aprotic solvents like DMSO in the presence of alkali base which gives a mixture of tetrahydro indole derivatives. The N-vinyl group of one of the derivatives can be cleaved to an NH-indole by using Hg(II) OAc followed by NaBH$_4$ reduction. Compounds of formula 24 can be obtained from compounds of formula 18 by reaction with dimethyl carbonate under appropriate baic conditions.

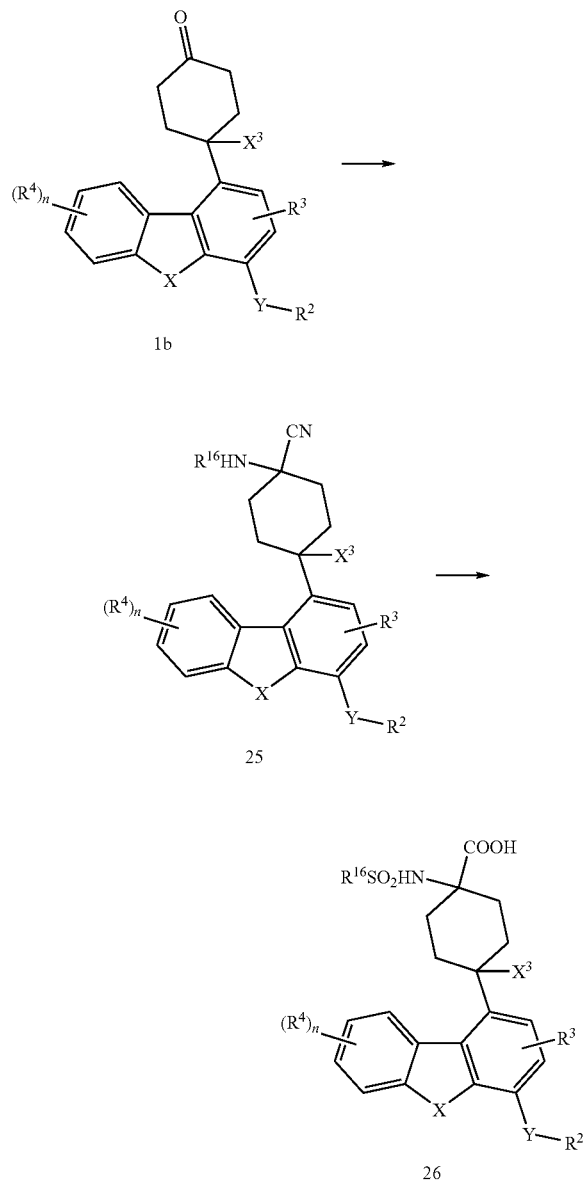

Compounds of formula 25 can be obtained from compounds of formula 1b by following the steps comprising reacting the cyclohexanone compound with an amine or substituted amine in the presence of sodium cyanide or potassium cyanide, followed by reacting the cyano compound thus formed with sulfonyl halides like tosyl or mesyl chlorides in the presence of a mild base like triethylamine followed by hydroxylation to form the final product 26.

It is understood that in any of the above schemes any reactive group in the substrate molecule may be protected according to any conventional procedure known in the prior art. Suitable protecting groups comprise tertiarybutyldimethylsilyl, methoxymethyl, triphenyl methyl, benzyloxycarbonyl, THP and the like for the protection of hydroxyl or phenolic hydroxy groups; N-Boc, N-Cbz, N-Fmoc, benzophenoneimine for the protection of amino or anilino groups, acetal protection for aldehydes and ketal protection for ketones. The methods of formation and removal of such protecting groups are conventional methods appropriate to the molecule being protected.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like, wherever applicable or chiral bases such as brucine, cinchona alkaloids and their derivatives and the like.

Different polymorphs of a compound of general formula I of present invention may be prepared by crystallization of the compound of formula I under different conditions. For example making use of commonly used solvents or their mixtures for recrystallization, crystallization at different temperature ranges, different cooling techniques like very fast to very slow cooling during crystallization procedure, by exposing to room temp, by heating or melting the compound followed by gradual cooling and the like. The presence of polymorphs may be determined by one or more methods like solid probe NMR spectroscopy, DSC, TGA, Powder X-Ray diffraction and IR.

In yet another embodiment of the present invention, the compounds may be purified by using techniques such as crystallization with solvents comprising at least one of the solvents like pentane, diethylether, isopropyl ether, chloroform, dichloromethane, ethylacetate, acetone, methanol, ethanol, isopropanol, water or their combinations or the compounds may be purified by column chromatography using alumina or silica gel and eluting the column with solvents such as hexane, petroleum ether, dichloromethane, chloroform, ethylacetate, acetone, methanol or combinations thereof.

The present invention also provides pharmaceutical compositions containing the compounds of the invention as defined above, it's derivatives, analogs, tautomeric forms, stereoisomers, bioisosters, polymorphs, enantiomers, diastereomers, pharmaceutically acceptable salts or pharmaceutically acceptable solvates in combination with suitable pharmaceutically acceptable carriers and diluents. The pharmaceutical compositions according to the present invention are useful for the treatment of allergic and inflammatory diseases including asthma, inflammatory diseases, allergic conditions, allergic conjunctivitis, eosinophilic granuloma, psoriasis, rheumatoid arthritis, diabetes, crohn's disease allergic rhinitis endotoxic shock and adult respiratory distress syndrome and related diseases. The pharmaceutical composition may be tablets, capsules, powders, syrups, solutions, suspensions, sprays and the like and they may contain flavorants, sweeteners etc. in a suitable solid or liquid carriers or diluents or in a suitable sterile media to form injectable solutions or suspensions. The active ingredient will be present in such pharmaceutical compositions in amounts sufficient to provide the desired dosage; such compositions may contain from 1 to 20% preferably 1 to 10% by weight of the active compound, the remainder of the composition being pharmaceutically acceptable carriers, diluents or solvents.

Suitable pharmaceutically acceptable carriers include solid fillers or diluents and sterile aqueous or organic solutions. Thus, for oral administration, the compounds can be combined with a suitable solid, liquid carrier or diluent to form capsules, tablets, powders, syrups, solutions, suspensions, sprays and the like. For oral administration, if a solid carrier is used the preparation may be in the form of a tablet, or may be placed in a hard gelatin capsule in powder or pellet form or it can be in the form of a troche or a lozenge. If liquid carriers are used, the preparation may be in the form of a syrup, emulsion, soft gelatin capsule or sterile injectable liquid such as an aqueous or non aqueous liquid suspension or solution. For nasal administration a liquid carrier in particular an aqueous carrier is used as an aerosol application. For parenteral application, particularly suitable compositions are injectable solutions or suspensions, preferably with sterile aqueous or organic media. The injectable solutions prepared in this manner can then be administered intravenously or intraperitonially. The formulation of the present invention is particularly significant for respiratory inhalation where the compounds of formula I is to be delivered in the form of aerosol under pressure. For inhalation formulation, the aerosol can be mixed with a gas or a liquid propellant for dispensing the active substances. Such devices are known in the priorart (e.g. from U.S. Pat. No. 6,273,086).

The invention also encompasses prodrugs of the compounds of the invention, which on administration undergo chemical conversion by metabolic processes before becoming active pharmacological substances. In general, such prodrugs will be functional derivatives of compounds of the invention, which are readily convertible in vivo into compounds of the invention.

The invention also encompasses the active metabolites of the compounds of the present invention of formula 1.

Bio Assay:

Phosphodiesterase assay is performed using recombinant human PDE enzymes expressed in a baculoviral system. These were tested for their similarity to PDE enzymes taken from human tissue using known inhibitor standards where available. Assay system is a modification of the two step method of Thompson and Appleman (Biochemistry 10; 311-316; 1971), adapted for the 96 well plate format. Prepared a stock of all the compounds in 100% DMSO at a concentration of 40 nM. Subsequent assays were performed in 5% DMSO. Inhibitor potency (% inhibition) of all compounds were tested at a final concentration of 1 μM in triplicate and for each enzyme, standard inhibitor Rolipram is included. $IC_{50}$ of each compound was tested by performing a 1 in 6 serial dilution at a starting concentration of 100 μM in triplicate.

The following examples are provided to enable one skilled in the art to practice the invention and are merely illustrative of the invention but do not limit the scope of the invention.

Example 1

Methyl 5-cyano-5-(4-methoxydibenzo[b,d]furan-1-yl)-2-oxocyclohexanecarboxylate

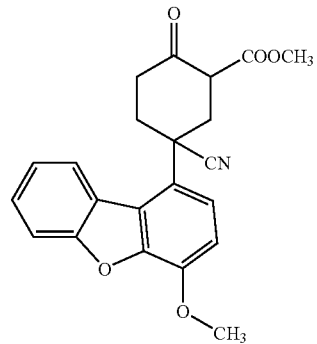

Step 1

To a solution of dibenzofuran (50 g, 0.29 mol) in 1000 ml dry diethyl ether and N,N,N',N'-tetramethylethane-1,2-diamine (70 ml, 0.43 mol) (TMEDA), 1.6M BuLi (235 ml, 0.32 mol) in hexanes was added with stirring under Nitrogen. The mixture was refluxed for 1 hour (yellow precipitate) and then cooled to 0° C. Tributyl borate (120 ml, 0.43 mol) was added until the precipitate disappeared. The reaction mixture is allowed to reach room temperature. After cooling again to 0° C., 125 ml of 30% hydrogen peroxide ($H_2O_2$) solution was added drop wise with vigorous stirring (light yellow precipitate). This mixture was refluxed for 1.5 hours, then cooled to 0° C. and acidified with 5M HCl. The organic phase was washed with cold 10% sodium sulphite solution and extracted with 2M sodium hydroxide. The combined aqueous extract was acidified, extracted with ethyl acetate and dried on sodium sulfate. Evaporation gave an orange oil which was filtered and isolated by column chromatography eluting with 15% ethyl acetate/hexane, yielding the product dibenzofuran-4-ol as an off-white solid. Yield 44 g (81%) $^1$H-NMR (300 MHz, $CDCl_3$) 7.95 (d, J=7.5, 1H); 7.60 (d, J=8.4, 1H); 7.53 (dd, J=7.8, 1H); 7.48 (t, J=8.4, 1.2, 1H); 7.36 (t, J=7.5, 1.2, 1H); 7.23 (t, J=7.8, 1H); 7.03 (dd, J=8.1, 1.0, 1H); 5.50 (s, OH)

Step 2

To a solution of 50% NaH (15.6 g, 0.32 mol) in DMF (100 ml), a solution of dibenzofuran-4-ol (40 g, 0.217 mol) in DMF (200 ml) was added drop wise at 0-5° C. under stirring and under a nitrogen atmosphere. The reaction mass was allowed to stir for 15 min at a temperature of 0-5° C. under $N_2$. A solution of methyl iodide (20.3 ml, 0.32 mol) in DMF (50 ml) was added drop wise at 0-5° C. and the reaction mass was allowed to stir for 1 hr at room temperature. When TLC confirmed absence of starting material, the reaction mass was quenched with water and extracted with ethyl acetate. The organic layer was dried with sodium sulfate and evaporated under vacuum to give product 4-Methoxydibenzofuran. Yield 43 g (98%)

$^1$H-NMR (300 MHz, $CDCl_3$) 7.95 (d, J=7.5, 1H); 7.64 (d J=8.4, 1H); 7.5 (d J=7.8, 1H); 7.48 (t, J=7.2, 1.2, 1H) 7.36 (t, J=7.2, 0.9, 1H); 7.29 (t, J=7.8, 1H); 7.01 (dd. J=8.1, 0.9, 1H) 4.08 (s, MeO, 3H)

Step 3

4-Methoxydibenzofuran (25 g, 0.12 mol) was dissolved in DCM (300 ml) at room temperature and cooled to 0° C. To this solution TiCl$_4$ (22.2 ml, 0.20 mol) was added drop wise at 0-2° C. The reaction mass was allowed to stir for 10 min and to that solution dichloromethyl methylether (9.7 ml, 0.107 mol) was added drop wise at 0° C. The reaction mass was stirred for 10 min and the reaction was monitored by TLC. Once the reaction was completed, the reaction mass was quenched with water and the organic layer was washed with NaHCO$_3$ solution and brine. The organic layer was dried with sodium sulfate and concentrated under vacuum. 4-methoxy-dibenzofuran-1-carbaldehyde was isolated by column chromatography obtaining a white solid. Yield 13.5 g (48%)

$^1$H-NMR (300 MHz, CDCl$_3$) 10.24 (s, 1H); 9.01 (d, J=8.5, 1H); 7.86 (d, J=8.5, 1H); 7.65 (d, J=8.3, 1H); 7.62 (t, J=7.2, 1H); 7.47 (t, J=7.2, 1H); 7.14 (d, J=8.3, 1H); 4.10 (s, 3H)

Step 4

To a solution of 4-methoxy-dibenzofuran-1-carbaldehyde (13.5 g, 0.059 mol) in acetonitrile (200 ml) was added LiBr (9.8 g, 0.13 mol) and TMS chloride (11.5 ml, 0.089 mol) at room temperature under stirring. The reaction mass was cooled to 0° C., and at 0° C., 1,1,3,3-tetramethyl disiloxane (17 ml, 0.096 mol) was added drop wise. The reaction mass was allowed slowly to come to room temperature and was stirred for 4 hrs at room temperature. Once TLC confirmed the absence of starting material, the reaction mass was diluted with DCM (300 ml), and filtered through Hyflow. The filtrate was concentrated under vacuum and again dissolved in DCM and filtered. To the brown colored compound DMF (150 ml) was added and the reaction mass was stirred for 10 min, until it dissolved. To the solution NaCN (6.44 g, 0.131 mol) was added and the reaction mass was allowed to stir for 4 hrs at room temperature. The reaction mass was quenched with water and extracted with ethyl acetate. The organic layer was washed with brine, dried with sodium sulfate and concentrated under vacuum to get (4-methoxy-dibenzofuran-1-yl)-acetonitrile, Yield 12 g (85%) $^1$H-NMR (300 MHz, CDCl$_3$) 7.9 (d, J=7.2, 1H); 7.67 (d, J=8.2, 1H); 7.55 (ddd, J=1.2, 7.3, 8.5, 1H); 7.43 (ddd, J=1, 7.8, 8.5, 1H), 7.29 (d, J=8.2, 1H), 6.98 (d, J=8.2, 1H); 4.15 (s, 2H), 4.0 (s, 3H)

Step 5

To a solution of (4-methoxy-dibenzofuran-1-yl)-acetonitrile (7 g, 0.029 mol) in acetonitrile (200 ml), Triton B (2.7 ml, 0.0147 mol) was added under N$_2$ at RT. The reaction mass was heated to reflux and at reflux temperature methyl acrylate (28.25 ml, 0.295 mol) was added drop wise. The reaction mass was stirred for 4 hrs at 90° C. Once the product is formed, the reaction mass was diluted with ethyl acetate and concentrated under vacuum. 4-cyano-4-(4-methoxy-dibenzofuran-1-yl)-heptane dioic acid dimethyl ester was isolated by column chromatography. Yield 8 g (65%)

$^1$H-NMR (300 MHz, CDCl$_3$) 8.19 (d, J=8.0, 1H) 7.70 (d, J=8.0, 1H) 7.60-7.38 (m, 3H); 6.98 (d, J=8.4, 1H); 4.1 (s, 3H); 3.55 (s, 6H); 2.95-2.85 (m, 2H); 2.70-2.50 (m, 4H); 2.45-2.10 (m, 2H)

Step 6

To a mixture of 50% NaH (4.6 g, 0.097 mol) in dimethoxymethane (20 ml) at room temperature under nitrogen was added drop wise at room temperature and under nitrogen a solution of 4-cyano-4-(4-methoxy-dibenzofuran-1-yl)-heptane dioic acid dimethyl ester (13.3 g, 0.032 mol) in dimethoxymethane (130 ml). The reaction mass was allowed to stir for 3 hrs at room temperature. Once product is formed, the reaction mass was quenched with water and extracted with ethyl acetate. The organic layer was dried with sodium sulfate and concentrated under vacuum. 5-cyano-5-(4-methoxy-dibenzofuran-1-yl)-2-oxo-cyclohexane carboxylic acid methyl ester was isolated by column chromatography. Yield 9.8 g (80%)

$^1$H-NMR (300 MHz, CDCl$_3$) 12.34 (s, 1H); 8.17 (d, J=8.0, 1H); 7.71 (d, J=8.0, 1H); 7.55 (t, J=7.3, 1H); 7.42 (t, J=7.3, 1H); 7.33 (d, J=8.5, 1H); 6.99 (d, J=8.5, 1H); 4.1 (s, 3H); 3.8 (s, 3H), 3.60-3.25 (m, 2H); 2.6-2.4 (m, 3H)

Example 2

1-(4-Methoxydibenzo[b,d]furan-1-yl)-4-oxocyclohexanecarbonitrile

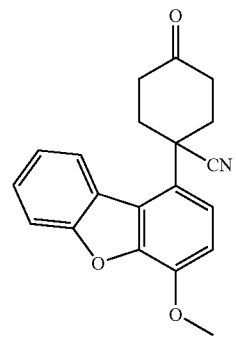

To a solution of 5-cyano-5-(4-methoxy-dibenzofuran-1-yl)-2-oxo-cyclohexane carboxylic acid methyl ester obtained in example 1 (7 g, 0.0185 mol) in DMSO (140 ml) and water (9 ml) was added sodium chloride (7 g, 0.119 mol) at room temperature. The reaction mass was heated to 130-140° C. for 5 hrs. Once the product is formed, the reaction mass was quenched with water and extracted with ethyl acetate. The organic layer was dried with sodium sulfate and concentrated under vacuum. 1-(4-methoxy-dibenzofuran-1-yl)-4-oxo-cyclohexane carbonitrile was isolated by column chromatography. Yield 4.2 g (71%)

M.P. 199.4-202° C.; $^1$H-NMR (300 MHz, CDCl$_3$) 8.25 (d, J=8.0, 1H); 7.72 (d, J=8.0, 1H); 7.53 (t, J=8.0, 1H); 7.47 (t, J=8.0, 1H); 7.26 (d, J=8.5, 1H); 7.00 (d, J=8.0, 1H); 4.1 (s, 3H); 3.15-2.90 (m, 4H); 2.70-2.60 (m, 2H); 2.40-2.30 (m, 2H)

Example 3

4-Cyano-4-(4-methoxydibenzo[b,d]furan-1-yl)cyclohexanecarboxylic acid

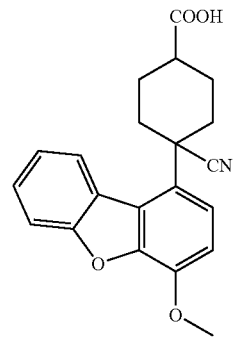

Step 1

At room temperature, to a solution of 1-(4-methoxy-dibenzofuran-1-yl)-4-oxo-cyclohexane carbonitrile (1 g, 0.003 mol), as obtained in example 2, in dry THF (15 ml), was added methyl dichloroacetate (0.48 ml, 0.0047 mol). The reaction mass was cooled to 0° C., Sodium methoxide (0.254 g, 0.0047 mol) was added portion wise and the reaction mass was allowed to stir for 1 hr at room temperature. Once the product is formed, the reaction mass was quenched with water and extracted with ethyl acetate to give 2-chloro-6-cyano-6-(4-methoxy-dibenzofuran-1-yl)-1-oxa-spiro[2.5]octane-2-carboxylic acid methyl ester, Yield 0.950 g (95%)

$^1$H-NMR (300 MHz, CDCl$_3$) 8.26 (d, J=8, 1H); 7.65 (d, J=7.6, 1H); 7.5 (m, 2H); 7.35 (m, 1H); 7.0 (d, J=8.5, 1H); 4.1 (s, 3H); 3.8 (s, 3H), 2.9-2.55 (m, 4H); 2.45-2.15 (m, 3H); 1.8-1.6 (m, 1H)

Step 2

At room temperature and under nitrogen, to a solution of 2-chloro-6-cyano-6-(4-methoxy-dibenzofuran-1-yl)-1-oxa-spiro[2.5]octane-2-carboxylic acid methyl ester (0.300 g, 0.0007 mol) (as obtained in step 1) in a mixture of ethanol (5 ml) and water (0.15 ml) was added sodium methoxide (0.190 g, 0.0035 mol). The reaction mass was refluxed for 1 hr, and once the product has formed, the reaction mass was brought to room temperature and the pH was adjusted to 2 with dil. HCl and extracted with Ethyl acetate. The organic layer was dried with sodium sulfate and concentrated under vacuum to get the 2-chloro-6-cyano-6-(4-methoxy-dibenzofuran-1-yl)-1-oxa-spiro[2.5]octane-2-carboxylic acid. Yield 0.180 g (64%)

$^1$H-NMR (300 MHz, DMSO) 8.2 (d, J=8.2, 1H); 7.82 (d, J=7.8, 1H), 7.62 (t, J=7.8, 1H); 7.51 (t, J=7.8, 1H); 7.48-7.33 (m, 1H), 7.28-7.19 (m, 1H), 4.1 (s, 3H); 2.8-2.2 (m, 6H); 1.45-1.21 (m, 2H)

Step 3

At room temperature, to a solution of the epoxy acid (0.380 g, 0.0009 mol) (as formed in step 2) in DMSO (8 ml)/Water (0.8 ml) sodium chloride (0.055 g, 0.000.9 mol) was charged and the reaction mass was heated to 100° C. for 7 hrs. Once the product has formed, the reaction mass was quenched with water and extracted with ethyl acetate. The organic layer was dried with sodium sulfate and concentrated under vacuum. 4-cyano-4-(4-methoxy-dibenzofuran-1-yl)-cyclohexane carboxylic acid was isolated by column chromatography. Yield 0.035 g, (10.8%)

M.P. 193.7-196.1° C.; $^1$H-NMR (300 MHz, CDCl$_3$) 8.28 (d, J=8.0, 1H); 7.69 (d, J=8.0, 1H); 7.52 (t, J=7.8, 1H); 7.43 (t, J=7.8, 1H); 7.21 (d, J=8.5, 1H); 6.96 (d, J=8.5, 1H); 4.1 (s, 3H); 2.99 (m, 1H); 2.72-2.60 (m, 2H); 2.45-2.20 (m, 4H); 2.15-2.05 (m, 2H)

Example 4

5-(4-Methoxydibenzo[b,d]furan-1-yl)-4,5,6,7-tetrahydro-2H-indazole-5-carbonitrile Step 1

At 0° C., to a solution of the cyclic ketone 1-(4-methoxy-dibenzofuran-1-yl)-4-oxo-cyclohexane carbonitrile (0.5 g, 0.00156 mol) (as obtained in example 2) in THF (15 ml) sodium methoxide (0.093 g, 0.0017 mol) was added and the reaction mass was stirred for 15 min. Then ethyl formate (0.15 ml, 0.0018 mol) was added at 0° C., and the reaction mass was refluxed for 1 hr. Once product has formed, reaction mass was quenched with water and extracted with ethyl acetate. The organic layer was dried with sodium sulfate and concentrated under vacuum. The product 5-ethynyl-5-(4-methoxy-dibenzofuran-1-yl)-2-oxo-cyclohexanecarbaldehyde was isolated by column chromatography. Yield 0.250 g (46%)

$^1$H-NMR (300 MHz, CDCl$_3$) 14.55 (s, 1H); 8.79 (s, 1H); 8.22 (d, J=7.9, 1H); 7.74 (d, J=7.4, 1H); 7.56 (t, J=7.4, 1H); 7.4 (t, J=7.4, 1H); 7.3 (d, J=8.5, 1H); 7.0 (d, J=8.5, 1H); 4.1 (s, 3H); 3.56-3.45 (m, 1H); 3.2-2.9 (m, 2H); 2.8-2.6 (m, 2H); 2.55-2.45 (m, 1H)

Step 2

To a solution of sodium hydroxide (0.030 g) in 5 ml of water, hydrazine hydrate (0.023 ml, 0.0004 mol) was charged at room temperature. The reaction mass was cooled to 5-10° C. and charged portion wise with the formyl compound 5-ethynyl-5-(4-methoxy-dibenzofuran-1-yl)-2-oxo-cyclohexanecarbaldehyde. The reaction mass was allowed to stir for 1 hr at room temperature. Once product has formed, the reaction mass was quenched with water and extracted with ethyl acetate. The organic layer was dried with sodium sulfate and concentrated under vacuum. The title product 5-(4-methoxy-dibenzofuran-1-yl)-4,5,6,7-tetrahydro-2H-indazole-5-carbonitrile was isolated by column chromatography. Yield 0.080 g (60%)

M.P. 171.2-174.6° C.; $^1$H-NMR (300 MHz, CDCl$_3$) 8.18 (d, J=7.9, 1H); 7.75 (d, J=7.9, 1H); 7.60-7.50 (m, 2H); 7.48-7.37 (m, 2H); 7.0 (d, J=8.5, 1H); 4.1 (s, 3H); 3.66 (d, J=16, 1H); 3.46 (d, J=16, 1H); 3.25 (ddd, J=8.8, 8.8, 16.5, 1H) 2.95 (ddd, J=4.2, 4.2, 8.7, 1H); 2.80-2.70 (m, 2H)

Example 5

N-[4-Cyano-4-(4-methoxydibenzo[b,d]furan-1-yl)cyclohexyl]methanesulfonamide

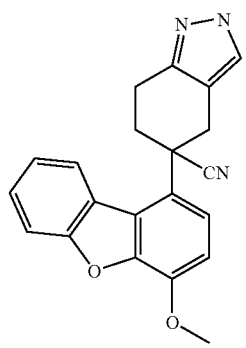

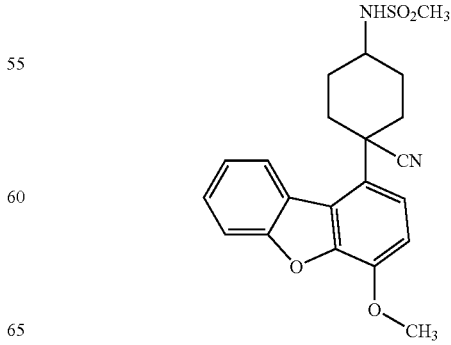

Step 1

At 0° C., to a mixture of cyclic ketone 1-(4-methoxy-dibenzofuran-1-yl)-4-oxo-cyclohexane carbonitrile (170 mg, 0.53 mmol) (as obtained in example 2) and R-Phenyl ethylamine (0.073 ml, 0.58 mmol) in 1,2-dichloroethane was added triacetoxyborohydride (160 mg, 0.8 mmol) over a period of 15 min. The reaction mixture was stirred at room temperature for another 2 h until TLC revealed complete consumption of the keto compound. The reaction mixture was cooled to ice bath temperature and basified by adding 10% aq. $NaHCO_3$ solution. The reaction mixture was extracted with $CHCl_3$, dried over anhydrous $Na_2SO_4$ and concentrated under reduced pressure to obtain crude product 1-(4-methoxy-dibenzofuran-1-yl)-4-(R)-1-phenyl-ethylamino)-cyclohexane carbonitrile, which was purified by column chromatography. Yield 200 mg (89%)

$^1$H-NMR (300 MHz, $CDCl_3$) 8.70 (d, J=8, 1H); 7.70 (d, J=8.0, 1H); 7.52 (t, J=7.2, 1H); 7.41 (t, J=8.1, 1H); 7.39-7.33 (m, 4H); 7.32-7.25 (m, 1H); 7.19 (d, 8.5, 1H); 6.94 (d, 8.5, 1H); 4.15-4.05 (m, 5H); 2.75-2.62 (m, 2H); 2.20-2.0 (m, 2H); 1.95-1.75 (m, 4H); 1.44 (d, J=6.5, 3H)

Step 2

To a solution of the phenyl ethyl amino compound obtained in step 1 (200 mg, 0.47 mmol) in methanol (5 ml) at room temperature was added $Pd(OH)_2$ (20% wet, 200 mg) and stirred under hydrogen atmosphere for 1 h until the TLC revealed complete disappearance of the starting material. The reaction mixture was filtered through a small pad of celite with the help of methanol. The filtrate was evaporated under reduced pressure and the crude mixture was column purified to obtain the amino compound 4-amino-1-(4-methoxy-dibenzofuran-1-yl)-cyclohexane carbonitrile Yield 80 mg (53%)

$^1$H-NMR (300 MHz, $CDCl_3$) 8.32 (d, 7.8, 1H); 7.71 (d, J=7.8, 1H); 7.55 (ddd, J=1.3, 7.8, 8.5, 1H); 7.46 (ddd, 1.3, 8.5, 9, 1H); 4.1 (s, 3H); 3.88-3.78 (m, 1H); 2.83-2.74 (m, 2H); 2.35-2.21 (m, 2H), 2.18-1.90 (m, 4H)

Step 3

To the solution of amino compound obtained in step 2 (70 mg, 0.22 mmol) in dry dichloromethane (2.2 ml) at 0° C. under $N_2$ atmosphere was added triethylamine (0.32 ml, 2.2 mmol) and N,N-dimethyl aminopyridine (DMAP, 3 mg), followed by methanesulfonyl chloride (0.06 ml, 0.66 mmol). The reaction mixture was stirred at room temperature for 2 h before being quenched by the addition of water. The two layers were separated and the aqueous layer was extracted with $CHCl_3$. The combined organic layer was dried over anhydrous $Na_2SO_4$ and the solvent was evaporated under vacuum to obtain a crude product which was purified by column chromatography to get pure N-[4-cyano-4-(4-methoxy-dibenzofuran-1-yl)cyclohexyl]-methane sulfonamide. Yield 70 mg M.P. 176.2-177.8° C.; $^1$H-NMR (300 MHz, $CDCl_3$) 8.26 (d, J=7.81H); 7.71 (d, J=7.81H); 7.54 (ddd, J=1.2, 7.2, 8.2 1H); 7.45 (ddd, J=1.2, 7.2, 8.2 1H); 7.21 (d, J=8.5 1H); 6.99 (d, J=8.5 1H); 4.88-4.75 (m, 1H); 4.10 (s, 3H); 3.11 (s, 3H), 2.90-2.80 (m, 2H); 2.50-2.30 (m, 4H); 2.05-1.90 (m, 2H)

Example 6

(3E)-3-[(Dimethylamino)methylene]-1-(4-methoxy-dibenzo[b,d]furan-1-yl)-4-oxocyclohexanecarbonitrile

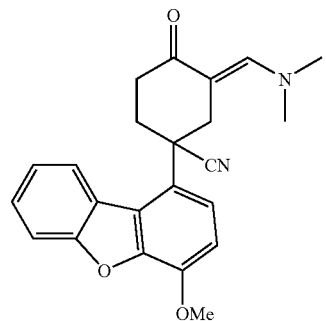

A solution of the compound obtained in example 2 (200 mg, 0.626 mmol), dimethylformamide dimethylacetal (447 mg, 3.76 mmol) and a catalytic amount of tetraethyl amine in benzene (15 ml) were distilled over a period of 3 hrs to about one half the original volume. Benzene (15 ml) was added to the reaction mixture and the distillation was continued. The process was repeated until the reaction showed absence of the ketone starting material. After all starting material was consumed, the solvent was completely evaporated under vacuum and residue was purified by column chromatography to give 174 mg (74.5% yields) of an off-yellow solid product. Melting point (MP)-decomposes at 300° C.

$^1$H-NMR (300 MHz, $CDCl_3$) 8.3 (d, J=7.93, 1H); 7.72 (d, J=7.32, 1H); 7.54 (t, J=7.3, 1H), 7.44 (t, J=7.2, 1H); 7.33 (d, J=8.5, 1H); 6.98 (d, J=8.5, 1H); 4.1 (s, 3H); 3.92 (d, J=14.7, 1H); 3.24 (d, J=14.9, 1H) 3.1 (s, 6H); 2.92-2.8 (m, 1H); 2.7-2.5 (m, 3H)

Example 7

Ethyl 6-cyano-6-(4-methoxydibenzo[b,d]furan-1-yl)-2-methyl-5,6,7,8-tetrahydro quinoline-3-carboxylate

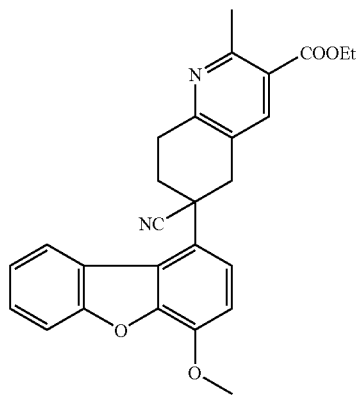

A mixture of the compound obtained in example 6 (300 mg, 0.8 mmol), ethylacetoacetate (114.4 mg, 0.88 mmol) and ammonium acetate (495 mg, 6.4 mmol) in acetic acid (25 ml) was stirred at 100-110° C. for 3 hrs under nitrogen atmosphere. The mixture was cooled to room temperature and diluted with 100 ml of water, then extracted with ethyl acetate (100 ml×2), washed with water, dried over sodium sulfate and concentrated under vacuum. The crude product was purified by column chromatography to give 120 mg (Yields 34.1%) of a yellow colored solid. MP-decomposes at 221.3° C.

$^1$H-NMR (300 MHz, CDCl$_3$), 8.28 (d J=7.83, 1H); 8.1 (s, 1H); 7.73 (d, J=7.98, 1H); 7.56 (t, J=7.2, 1H); 7.45 (t, J=7.2, 1H); 7.26 (d, 9.64, 1H); 6.96 (d, J=8.5, 1H); 4.4 (q, J=7.1, 2H); 4.1 (s, 3H); 3.85 (dd, J=16, 2H); 3.6-3.4 (m, 2H); 2.9-2.6 (m, 2H); 2.9 (s, 3H); 1.42 (t, 3H)

Example 8

5-(4-Methoxydibenzo[b,d]furan-1-yl)-1-phenyl-4,5,6,7-tetrahydro-1H-indazole-5-carbonitrile

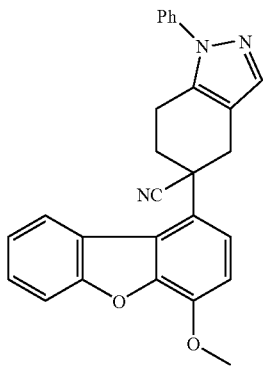

Example 9

5-(4-Methoxydibenzo[b,d]furan-1-yl)-2-phenyl-4,5,6,7-tetrahydro-2H-indazole-5-carbonitrile

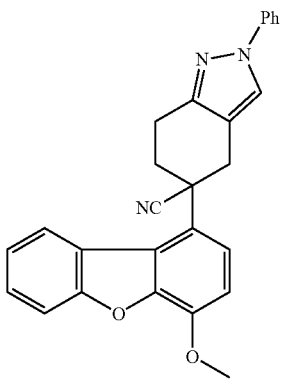

A mixture of compound obtained in example 7 (100 mg, 0.267 mmol) and phenyl hydrazine (35.7 mg, 0.33 mmol) in 10 ml of ethanol was stirred at room temperature for 18 hrs under nitrogen atmosphere. Ethanol was evaporated under reduced pressure and residue was partitioned between ethyl acetate (50 ml×2) and water (50 ml). The organic layer was washed with water followed by brine, dried over sodium sulfate and evaporated under vacuum. The crude was purified by column chromatography by eluting 20% ethyl acetate/hexane to give regeoisomeric mixture of products.

Example 8 was eluted at less polar, 32 mg (Yields-14.3%), MP-231-233° C.

$^1$H-NMR (300 MHz, CDCl$_3$) 8.23 (d, J=8, 1H); 7.73 (d, J=7.9, 1H); 7.84 (s, 1H); 7.7-7.3 (m, 7H); 7.44 (d, J=8.5, 1H); 7 (d, J=8.5, 1H); 4.1 (s, 3H); 3.7 (dd, J=16, 2H); 3.4-3.22 (m, 1H); 3.1-2.9 (m, 1H); 2.8-2.7 (m, 2H)

Example 9 was eluted at more polar, 68 mg (Yields-30.4%), MP-234.5-236° C.

$^1$H-NMR (300 MHz, CDCl$_3$) 8.2 (d, J=8, 1H); 7.73 (d, J=8.2, 1H); 7.64 (s, 1H); 7.6-7.35 (m, 7H); 7.4 (d, J=8.5); 7 (d, J=8.5 1H); 4.1 (s, 3H); 3.7-3.4 (dd, J=16, 2H); 3.4-3.24 (m, 1H); 2.9-2.82 (m, 1H); 2.75-2.6 (m, 2H)

Example 10

6-Cyano-6-(4-methoxydibenzo[b,d]furan-1-yl)-2-methyl-5,6,7,8-tetrahydro quinoline-3-carboxylic acid

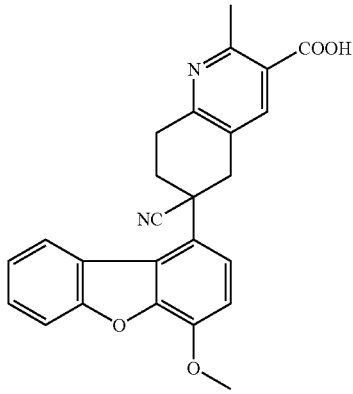

To a stirred solution of the compound obtained in example 7 (50 mg, 0.1135 mmol) in ethanol (2 ml), was added 2 N aqueous NaOH solution (2 ml) and the reaction mass was stirred at room temperature for 16 hrs. The solvent was evaporated under vacuum and the residue was diluted with water (10 ml). The basic aq. solution was washed with ether (10 ml×2), and acidified with 1N HCl solution to pH 2. The reaction mass was extracted with chloroform, the organic layer was washed with water (20 ml) followed by brine, dried over sodium sulfate and concentrated under vacuum, to give 40 mg (85% yields) of the product as a light yellow colored solid. MP-decomposes at 195.6° C.

$^1$H-NMR (300 MHz, DMSO-d$_6$) 8.27 (d, J=7.83); 8.1 (s, 1H); 7.85 (d, J=8, 1H); 7.63 (t, J=7.2, 1H); 7.54 (t, J=7.2, 1H); 7.35 (d, J=8, 6, 1H); 7.24 (d, J=8.6, 1H); 4.1 (s, 3H); 3.85-3.6 (dd, J=16, 2H); 3.2-3.1 (m, 2H); 3-2.8 (m, 2H)

Example 11

5-(4-Methoxydibenzo[b,d]furan-1-yl)-4,5,6,7-tetrahydro-2,1-benzisoxazole-5-carbonitrile

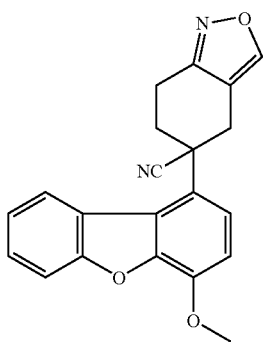

Hydroxylamine hydrochloride (20 mg, 0.3 mmole) was added to a stirred solution of sodium ethoxide (22 mg, 0.3 mmole) in 10 ml of ethanol and the compound as obtained in example 6 (75 mg, 0.2 mmole) in 5 ml of ethanol and the reaction mass was allowed to stir for 2 hrs at room temperature. The solvent was evaporated under vacuum and the residue was taken up in 50 ml of ethyl acetate and washed with water followed by brine. The organic layer was dried over on sodium sulfate and concentrated under vacuum. The crude product was purified by column chromatography to get 45 mg (65.4% yields) yellow colored solid.

MP-193.5-197° C.

$^1$H-NMR (300 MHz, CDCl$_3$); 8.24 (d, J=8, 1H); 7.73 (d, J=8, 1H); 7.6-7.4 (m, 3H,); 7.2 (d, J=8.5, 1H); 6.95 (d, J=8.4, 1H); 4.1 (s, 3H); 3.5 (m, 1H); 3 (m, 1H); 2.7 (m, 1H); 2.2 (m, 1H)

Example 12

5-(4-Methoxydibenzo[b,d]furan-1-yl)-3-oxo-3,3a,4,5,6,7-hexahydro-2H-indazole-5-carbonitrile

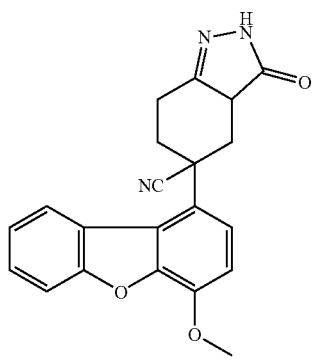

A mixture of compound as obtained in example 1 (50 mg, 0.1326 mmole), hydrazine hydrate (14 mg, 0.266 mmole) and triethylamine (40 mg, 0.4 mmole) in methanol (5 ml) was stirred at 60-70° C. for 45 min. Methanol was evaporated under vacuum and the residue was partitioned between ethyl acetate (20 ml) and water (20 ml). The ethyl acetate layer was washed with water followed by brine, and the organic layer was evaporated under vacuum to get 42 mg (88.2% yields) product.

MP-more than 300° C.

$^1$H-NMR (300 MHz, CDCl$_3$); 11.4 (s, 1H); 8.13 (d, J=7.6, 1H); 7.8 (d, J=7.6, 1H); 7.62 (t, J=7.2, 1H); 7.5 (t, J=7.1, 1H); 7.4 (d, J=8.5, 1H); 7.2 (d, J=8.6, 1H); 4.1 (s, 3H); 3.1-2.4 (m, 6H)

Example 13

6-(4-Methoxydibenzo[b,d]furan-1-yl)-4-oxo-3,4,5,6,7,8-hexahydroquinazoline-6-carbonitrile

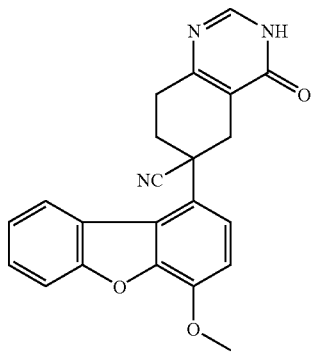

To a stirred solution of sodium methoxide (185.3 mg, 3.5 mmol) in 10 ml of methanol was added formamidine acetate (290 mg, 2.78 mmol) and the compound obtained in example 1. The reaction mass was allowed to stir at 60-70° C. for 18 hrs under nitrogen atmosphere. Most of the methanol was evaporated under vacuum and residue was purified by column chromatography to get 200 mg (67.3% yields) of the product.

$^1$H-NMR (300 MHz, DMSO-d$_6$); 12.6 (s, 1H); 8.2 (d, J=7.88, 1H); 8.14 (s, 1H); 7.85 (d, J=8, 1H); 7.63 (t, J=7.5, 1H); 7.52 (t, J=7.5, 1H); 7.36 (d, J=8.5, 1H); 7.26 (d, J=8.6, 1H); 4.1 (s, 3H); 3.6 (m, 1H); 3.2-2.9 (m, 3H); 2.8-2.7 (m, 2H)

Example 14

6-(4-Methoxydibenzo[b,d]furan-1-yl)-3-methyl-4-oxo-3,4,5,6,7,8-hexahydroquinazoline-6-carbonitrile

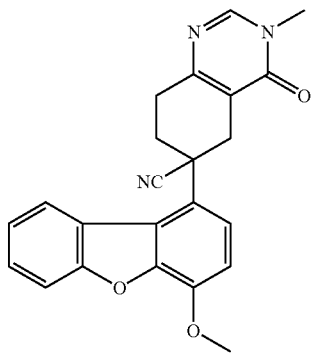

To a well stirred slurry of compound obtained in example 13 (75 mg, 0.2 mmol) and cesium carbonate (73 mg, 0.22 mmol) in dry DMF (5 ml) was added iodomethane (36.92 mg, 0.26 mol) and the mixture was allowed to stir for 1 hr at room temperature under nitrogen atmosphere. The reaction mixture was quenched with ice water (50 ml), and then extracted with ethyl acetate (50 ml). The organic layer was washed with water followed by brine and dried over sodium sulfate. The organic layer was concentrated under vacuum and the crude product was purified by column chromatography to get 40 mg of the pure product (Yields-52%) MP-235.4-240.8° C.

$^1$H-NMR (300 MHz, CDCl$_3$); 8.22 (d, J=7.8, 1H); 8.1 (s, 1H); 7.71 (d, J=8, 1H); 7.53 (t, J=8, 1H); 7.43 (t, J=8, 1H); 7.33 (d, 8.5, 1H); 7 (d, J=8.5, 1H); 4.1 (s, 3H); 3.75 (d, J=8.5, 1H); 3.6 (s, 3H); 3.6-3.5 (m, 1H); 3.3-3.2 (m, 2H); 2.9-2.7 (m, 2H)

Example 15

6-(4-Methoxydibenzo[b,d]furan-1-yl)-5,6,7,8-tetrahydroquinazoline-6-carbonitrile

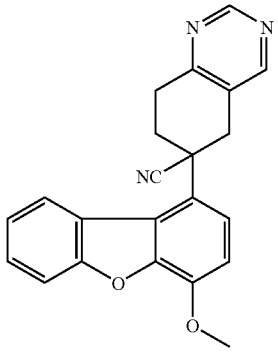

A solution of compound as obtained in example 6 (100 mg, 0.267 mmol) and formamdine acetate (39 mg, 0.373 mmol) in dry ethanol (4 ml) was stirred at 70-80° C. for 2 hrs. The solvent was evaporated under vacuum and the crude product was purified by column chromatography to get 35 mg of the product (Yields-14.76%) MP-213.8-215.2° C.

$^1$H-NMR (300 MHz, CDCl$_3$); 9.1 (s, 1H); 8.6 (s, 1H); 8.24 (d, J=8, 1H); 7.73 (d, J=8.2, 1H); 7.55 (t, J=7.2, 1H); 7.44 (t, J=7.4, 1H); 7.23 (d, J=8, 1H); 6.98 (d, J=8, 1H); 4.1 (s, 3H); 3.83 (d, J=16, 1H); 3.6-3.4 (m, 2H); 3.2-3.0 (m, 1H); 3-2.9 (m, 1H); 2.7-2.6 (m, 1H)

Example 16

2-Amino-6-(4-methoxydibenzo[b,d]furan-1-yl)-4-oxo-3,4,5,6,7,8-hexahydroquinazoline-6-carbonitrile

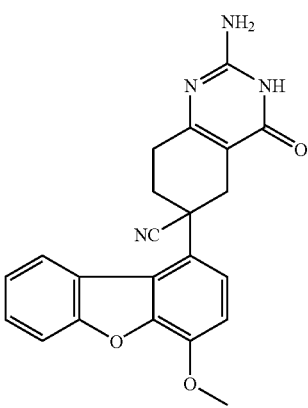

A mixture of the compound obtained in example 1 (200 mg, 0.53 mmol), guanidine HCl (127 mg, 1.326 mmol) and sodium methoxide (100 mg) in 2 ml methanol was stirred overnight at room temperature. The solvent was evaporated under vacuum and the crude residue was purified by column chromatography to get 150 mg (73.3% yields) as a white solid product. MP-decomposes at 300° C.

$^1$H-NMR (300 MHz, DMSO-d$_6$); 11(s, 1H); 8.1 (d, J=8, 1H); 7.82 (d, J=8.2, 1H); 7.64 (t, J=7.4, 1H); 7.5 (t, J=7.5, 1H); 7.32 (d, J=8.55, 1H); 7.2 (d, J=8.55, 1H); 4.1 (s, 3H); 3.5 (m, 2H); 2.9-2.8 (m, 2H); 2.74-2.6 (m, 1H); 2.5-2.32 (m, 1H)

Example 17

2-Amino-6-(4-methoxydibenzo[b,d]furan-1-yl)-5,6,7,8-tetrahydroquinazoline-6-carbonitrile

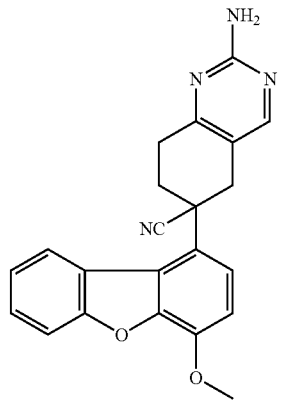

A mixture of the compound obtained in example 6 (100 mg, 0.267 mmol), guanidine HCl (33.5 mg, 0.35 mmol) and sodium ethoxide (25 mg, 0.35 mmol) in 5 ml ethanol was heated at 70-80° C. for 1 hr. The mixture was cooled to room temperature and the solvent was evaporated under vacuum. The crude residue was purified by column chromatography to get 80 mg (81% yields) of a white colored solid product.

MP-decomposes at 300° C.

$^1$H-NMR (300 MHz, DMSO-d$_6$); 8.24 (d, J=7.9, 1H); 8.2 (s, 1H); 7.85 (d, J=8, 1H); 7.63 (t, J=7.4, 1H); 7.5 (t, J=7.8, 1H); 7.38 (d, J=8.5, 1H); 7.25 (d, J=8.6, 1H); 6.55 (s, 2H); 4.1 (s, 3H); 3.6 (d, J=15.5, 1H); 3.4 (d, J=15, 1H); 3.1-3 (m, 1H); 2.9-2.7 (m, 3H)

Example 18

{[6-Cyano-6-(4-methoxydibenzo[b,d]furan-1-yl)-5,6,7,8-tetrahydroquinazolin-2-yl]amino}acetic acid

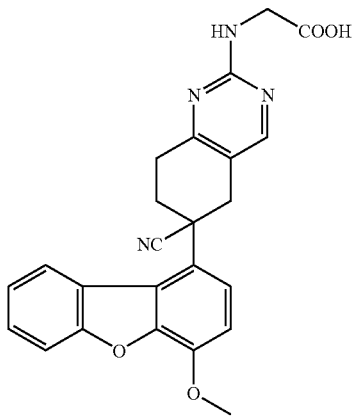

A mixture of the compound obtained in example 6 (100 mg, 0.267 mmol), guanidine acetic acid and sodium hydroxide (54 mg, 1 mol) in 10 ml of methanol was stirred at 60-70° C. for 8 hrs. Methanol was evaporated under vacuum and the reaction mass was diluted with 10 ml of water. The aqueous layer was washed with ether, acidified with 0.1 N HCl to pH 2 and extracted with ethyl acetate. The organic layer was washed with water followed by brine, and concentrated under vacuum. The crude product was crystallized form hexane to give 60 mg (52.45% yields) of a yellow colored solid.

$^1$H-NMR (300 MHz, DMSO-$d_6$); 8.24 (d, J=6.4, 1H); 8.2 (s, 1H); 7.85 (d, J=8.1, 1H); 7.63 (t, J=7.6, 1H); 7.53 (t, J=7.4, 1H); 7.38 (d, J=8.5, 1H); 7.25 (d, J=8.5, 1H); 6.67 (s, 1H); 4.1 (s, 3H); 3.7 (s, 2H); 3.7-3.5 (m, 2H); 3-3.2 (m, 2H); 2.9-2.8 (m, 2H)

Example 19

Ethyl [6-cyano-6-(4-methoxydibenzo[b,d]furan-1-yl)-4-oxo-5,6,7,8-tetrahydroquinazolin-3(4H)-yl]acetate

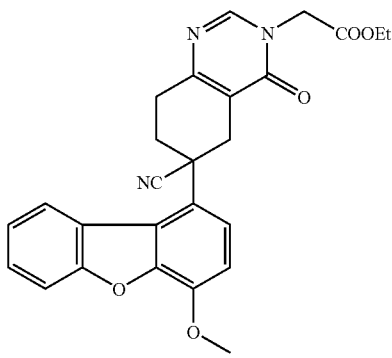

To a solution of the compound obtained in example 13 (170 mg, 0.46 mmol) in 5 ml of dry DMF was added ethyl bromoacetate (84.5 mg, 0.5 mmol) and cesium carbonate (195.6 mg, 0.6 mmol) at room temperature for 1 hr. Once the reaction has completed, the reaction mass was diluted with water and extracted with ethyl acetate. The organic layer was washed with water, followed by brine, and concentrated under vacuum. The crude product was purified by column chromatography to get 175 mg (83.2% yields) of the product. MP-106.2-125.1° C.

$^1$H NMR (300 MHz, CDCl$_3$); 8.2 (d, J=7.9, 1H); 8 (s, 1H); 7.7 (d, J=8, 1H); 7.8 (t, J=7.2, 1H); 7.43 (t, J=8, 1H); 7.3 (d, J=8.5, 1H); 7 (d, J=8.5, 1H); 4.8-4.5 (d d, J=16.8, 2H); 4.3 (q, J=7, 2H); 4.1 (s, 3H); 3.7 (d, J=18, 1H); 3.4-3.1 (m, 2H); 2.9-2.8 (m, 3H); 1.4-1.3 (t, J=7, 3H)

Example 20

[6-Cyano-6-(4-methoxydibenzo[b,d]furan-1-yl)-4-oxo-5,6,7,8-tetrahydroquinazolin-3(4H)-yl]acetic acid

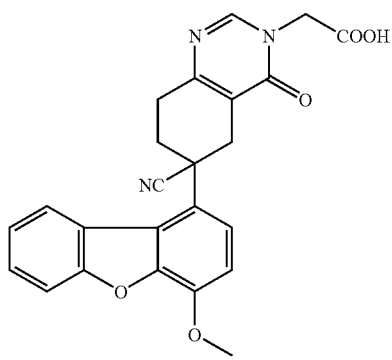

To a stirred solution of the compound obtained in example 19 (100 mg, 0.2188 mmol) in 4 ml of ethanol was added 1N NaOH solution (3 ml) and the reaction mass was allowed to stir at room temperature for 4 hrs. The reaction mass was diluted with 20 ml water and washed 3 timed with 25 ml diethyl ether. The aqueous layer was acidified with 1N aq. HCl to pH 2-3 and extracted with chloroform. The organic layer was washed with water followed by brine, and concentrated under vacuum. The residue was triturated with ether to give 45 mg (Yields-48%) of product.

$^1$H-NMR (300 MHz, DMSO-$d_6$); 8.24 (d, J=8.2, 1H); 8.15 (s, 1H); 7.84 (d, J=8, 1H); 7.63 (t, J=7.3, 1H); 7.52 (t, J=7.4, 1H); 7.37 (d, J=8.6, 1H); 7.24 (d, J=8.6, 1H); 4.5 (s, 2H); 4.1 (s, 3H); 3.6 (m, 1H)

Example 21

6-(4-Methoxydibenzo[b,d]furan-1-yl)-2-methyl-4-oxo-3,4,5,6,7,8-hexahydroquinazoline-6-carbonitrile

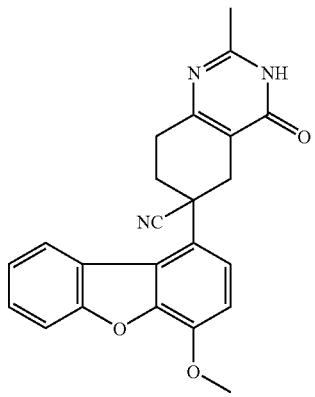

To a mixture of the compound obtained in example 1 (200 mg, 0.53 mol), acetamidine HCl (124.5 mg, 1.32 mmol) and sodium methoxide (98.3 mg, 1.85 mmol) in 7 ml of methanol was stirred at 60-70° C. for 18 hrs under nitrogen atmosphere. Once the reaction is complete, the reaction mass was evaporated under vacuum and the residue was diluted with ethyl acetate and water. The organic layer was washed with water followed by brine, dried over sodium sulfate and concentrated under vacuum. The crude product was purified by column chromatography to get 200 mg (40% yields) of the solid product. MP-more than 300° C.

$^1$H-NMR (300 MHz, DMSO-$d_6$); 12.5 (s, 1H); 8.2 (d, J=8, 1H); 7.85 (d, J=8, 1H); 7.64 (t, J=7.5, 1H); 7.5 (t, J=7.4, 1H); 7.34 (d, J=8.6, 1H); 7.24 (d, J=8.6, 1H); 4.1 (s, 3H); 3.6 (m, 1H); 3 (m, 3H); 2.8-2.6 (m, 2H), 2.3 (s, 3H)

Example 22

Ethyl [6-cyano-6-(4-methoxydibenzo[b,d]furan-1-yl)-2-methyl-4-oxo-5,6,7,8-tetrahydro quinazolin-3(4H)-yl]acetate

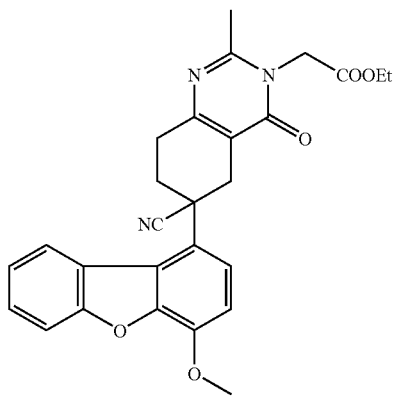

Example 23

Ethyl {[6-cyano-6-(4-methoxydibenzo[b,d]furan-1-yl)-2-methyl-5,6,7,8-tetrahydro quinazolin-4-yl]oxy}acetate

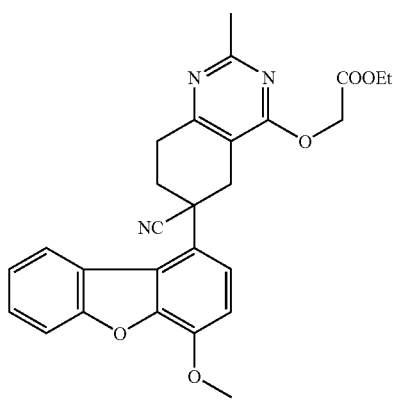

To a solution of the compound obtained in example 21 (150 mg, 1.76 mmles) in dry DMF (5 ml) was added ethylbromoacetate (322.3 mg, 1.93 mmol) and cesium carbonate (688 mg, 2.11 mmol). The reaction mass was stirred at room temperature for 1 hr, diluted with water and extracted with ethyl acetate. The organic layer was washed with water followed by brine and dried over sodium sulfate and concentrated under vacuum. The crude product was purified by column chromatography to get both pure compounds.

Example 22 is eluted at less polar, 50 mg (Yields-27.2%), MP-165.1-175° C.

$^1$H NMR (300 MHz, CDCl$_3$); 8.24 (d, J=8, 1H); 7.72 (d, J=8.1, 1H); 7.55 (t, J=7.4, 1H); 7.44 (t, J=7.5, 1H); 7.28 (d, J=9, 1H); 6.98 (d, J=8.5, 1H); 5.1-4.8 (d d, J=15.6, 2H); 4.24 (q, J=7.1, 2H); 4.1 (s, 3H); 3.8-3.6 (d d, J=17.3, 2H); 3.4-3.2 (m, 1H); 2.9-2.6 (m, 3H); 2.52 (s, 3H)

Example 23 is eluted at more polar, 30 mg (Yields-16.34%), MP-116.2-140° C.

$^1$H NMR (300 MHz, CDCl$_3$); 8.23 (d, J=8, 1H); 7.7 (d, J=8, 1H); 7.54 (t, J=7.3, 1H); 7.4 (t, J=7.3, 1H); 7.28 (d, J=8.5, 1H); 6.96 (d, J=8.5, 1H); 5 (d, J=17.3, 1H); 4.7 (d, J=17.3, 1H); 4.3 (q, J=7, 1H); 4.1 (s, 3H); 3.7 (m, 1H); 3.3-3.0 (m, 2H); 2.9-2.8 (m, 2H); 2.5 (m, 1H); 2.5 (s, 3H); 1.35 (t, J=3H)

Example 24

1-(4-Methoxydibenzo[b,d]furan-1-yl)-4-(methoxyimino)cyclohexanecarbonitrile

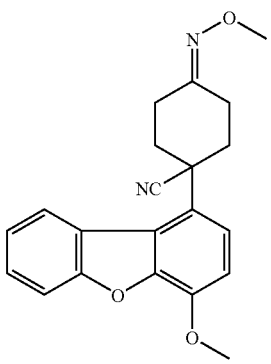

Step 1—A mixture of the compound obtained in example 2 (50 mg, 0.156 mmole), sodium acetate (20 mg, 0.238 mmol) and hydroxylamine hydrochloride (17 mg, 0.235 mmol) in 2 ml of ethanol was refluxed for 3 hrs at 85-90° C. Once the reaction has completed, ethanol was distilled off, the reaction mass was diluted with water, neutralized with sodium bicarbonate and extracted with ethyl acetate. The ethyl acetate layer was evaporated under vacuum to get 45 mg of the oxime product (Yields-86.5%)

Step 2—Under nitrogen atmosphere, to a solution of 50% sodium hydride (24 mg, 0.2 mmol) in 2 ml of dry DMF a solution of the oxime product in dry DMF was added drop wise. The reaction mass was allowed to stir for 30 minutes at room temperature. A solution of methyl iodide added drop wise and the reaction mass was allowed to stir for 30 minutes. Once the reaction has completed, the reaction mass was quenched with water and extracted with ethyl acetate. The organic layer was dried over sodium sulfate and evaporated under vacuum to get the product 30 mg (Yields-65%)

$^1$H NMR (300 MHz, CDCl$_3$); 8.27 (d, J=7.8, 1H); 7.73 (d, J=7.5, 1H); 7.55 (d d d, J=1.2, 7.3, 8.2, 1H); 7.46 (m, 1H); 7.26 (d, J=8.4,); 7 (d, J=8.5, 1H); 4.1 (s, 3H); 3.9 (s, 3H); 3.6 (m, 1H); 3-2.6 (m, 4H); 2.5 (m, 1H); 2.2-2.1 (m, 2H)

Example 25

({[4-Cyano-4-(4-methoxydibenzo[b,d]furan-1-yl)cyclohexylidene]amino}oxy)acetic acid

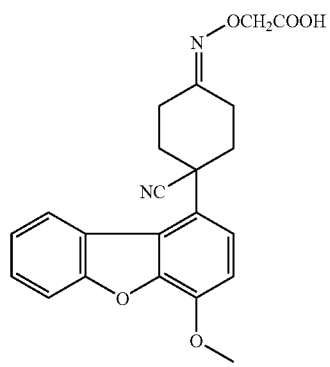

Step 1—A mixture of the compound obtained in example 2, (500 mg, 1.56 mmole), sodium acetate (190 mg, 2.38 mmol) and hydroxylamine hydrochloride (163 mg, 2.35 mmol) in 10 ml of ethanol was refluxed for 3 hrs at 85-90° C. Once the reaction has completed, ethanol was distilled off, the reaction mass was diluted with water, neutralized with sodium bicarbonate and extracted with ethyl acetate. The ethyl acetate layer was evaporated under vacuum to get 500 mg of the oxime product (Yields-95.6%)

Step 2—To a mixture of the oxime product (500 mg, 1.49 mol), ethylbromoacetate (324 mg, 1.9 m mol) and potassium carbonate (61 mg, 0.5 mmol) in dry DMF was heated to 60-70° C. for 2 hrs. Once the reaction has completed, the reaction mass was diluted with water and extracted with ethyl acetate. The organic layer was dried over sodium sulfate and evaporated under vacuum to get 250 mg (Yields-40%) of the ester product.

Step 3—To a solution of above ester product (200 mg, 0.47 mmol) in 3.5 ml of ethanol was added solution of NaOH (28.5 mg, 0.71 mmol) dissolved in 1 ml of water. The reaction mass was stirred overnight at room temperature. Once the reaction has completed, ethanol was evaporated under vacuum and the reaction mass was acidified with conc. HCl to pH 2 and extracted with ethyl acetate. The organic layer was dried over sodium sulfate and evaporated under vacuum to get 40 mg of acid product (Yields-22.2%).

$^1$H NMR (300 MHz, CDCl$_3$); 11.4 (s, 1H); 8.13 (d, J=7.6, 1H); 7.8 (d, J=7.6, 1H); 7.62 (t, J=7.2, 1H); 7.5 (t, J=7.1, 1H); 7.4 (d, J=8.5, 1H); 7.2 (d, J=8.6, 1H); 4.1 (s, 3H); 3.1-2.4 (m, 6H)

The invention claimed is:
1. A compound of formula

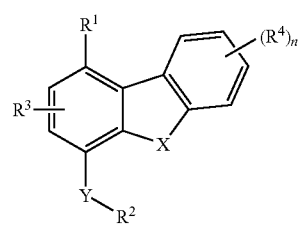

(I)

and its tautomers, stereoisomers, enantiomers, diastereomers, and pharmaceutically acceptable salts wherein
R$^1$ is

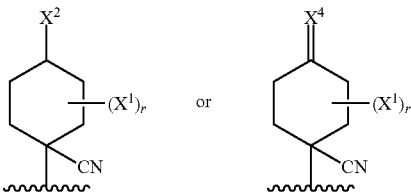

X$^1$ is selected from hydrogen, optionally substituted alkyl, optionally substituted N,N-dimethylaminoalkenyl, carboxy, =CH—NR$^5$R$^6$, COOR$^6$;

X$^2$ is selected from optionally halo, cyano, carboxy, COOR$^6$, substituted alkyl, NR$^5$R$^6$, —NR$^5$S(O)$_m$R$^6$;

X$^4$ represents O, S, NR$^5$, N—OR$^5$, =N—OCH$_2$COOH, =N—O-Me;

when X$^1$ and X$^2$ or X$^1$ and X$^4$; are ortho to each other, they may together form a 4 to 7 membered ring system selected from an alicyclic or heterocyclic ring;

r is 0 or 1;

R$^2$ represents optionally substituted groups selected from alkyl, haloalkyl, alkenyl, alkynyl, optionally substituted cycloalkyl, optionally substituted aryl, optionally substituted heteroaryl or optionally substituted heterocyclyl;

R$^5$ represents hydrogen, alkoxy, R'COOR$^6$, optionally substituted alkyl or optionally substituted aryl;

R$^6$ represents hydrogen, optionally substituted alkyl or optionally substituted aryl;

R$^5$ and R$^6$ may together form a 3 to 12 membered mono or polycyclic ring;

R' represents a direct bond or an optionally substituted alkylene;

m is an integer represented by 0, 1 or 2.

2. The compound of claim 1 wherein R$^1$ is

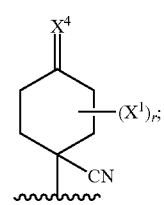

X$^1$ is COOR$^6$; X$^4$ is O; r=1; and R$^2$ and R$^6$ are methyl.

3. The compound of claim 1 wherein the 4 to 7 membered ring system selected form an alicyclic or heterocyclic ring is optionally mono- or di-substituted with oxo, carboxy, R'COOR$^6$, R'NR$^5$R$^6$, OR$^5$, alkyl or aryl, wherein R' is a direct bond or an optionally substituted alkylene.

4. The compound according to claim 1, wherein $X^1$ is $COOR^6$.

5. The compound according to claim 1, wherein $X^1$ is N,N-dimethylaminoalkenyl.

6. The compound according to claim 1, wherein $X^2$ is $COOR^6$.

7. The compound according to claim 1, wherein $X^2$ is $NR^5S(O)_mR^6$.

8. The compound according to claim 7, wherein $R^5$ is hydrogen, m is 2 and $R^6$ is methyl.

9. The compound according to claim 1, wherein $X^1$ and $X^2$ or $X^1$ and $X^4$ are ortho to each other and together fog n a 4 to 7 membered ring system selected from an alicyclic or heterocyclic ring.

10. The compound according to claim 1 or 9, wherein the 4 to 7 membered ring system is selected from

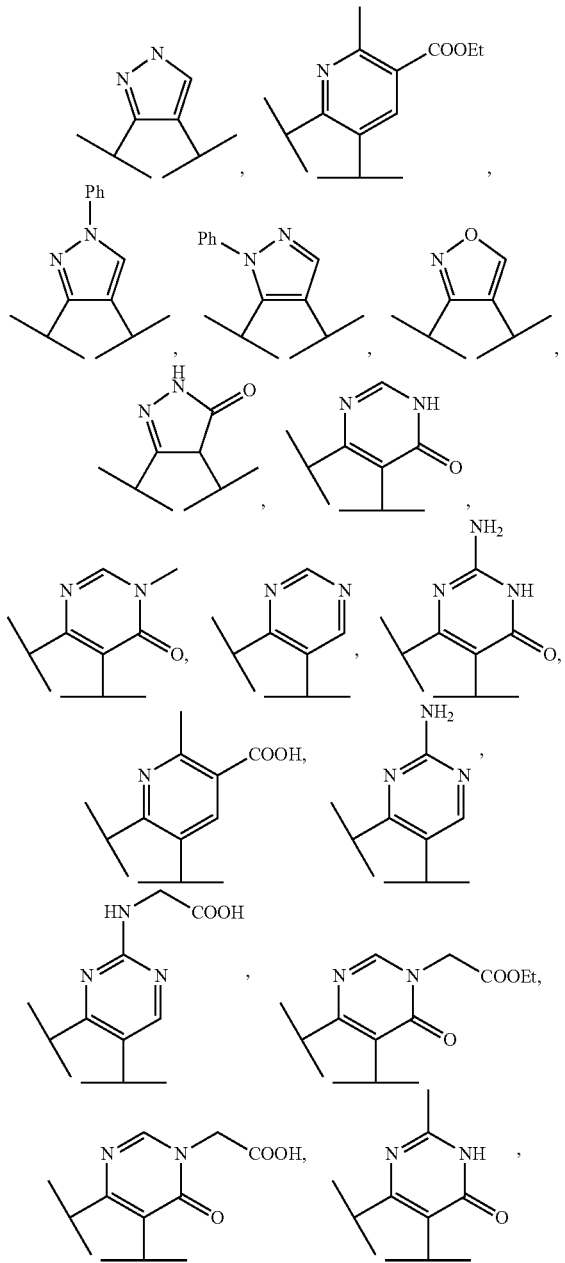

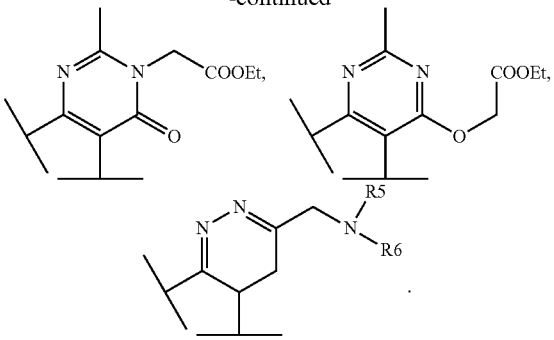

11. The compound according to claim 1, wherein $X^4$ is O.

12. The compound according to claim 1, wherein $X^4$ is $N-OR^5$ wherein $R^5$ is alkoxy.

13. The compound according to claim 1, wherein $X^4$ is =N—OCH$_2$COOH.

14. The compound according to claim 1, wherein $R^2$ is methyl.

15. A compound according to claim 1, wherein the compound is selected from
  Methyl-5-cyano-5-(4-methoxydibenzo[b,d]furan-1-yl)-2-oxocyclohexane carboxylate,
  1-(4-Methoxydibenzo[b,d]furan-1-yl)-4-oxocyclohexanecarbonitrile,
  4-Cyano-4-(4-methoxydibenzo[b,d]furan-1-yl)cyclohexanecarboxylic acid,
  5-(4-Methoxydibenzo[b,d]furan-1-yl)-4,5,6,7-tetrahydro-2H-indazole-5-carbonitrile,
  N-[4-Cyano-4-(4-methoxydibenzo[b,d]furan-1-yl)cyclohexyl]methanesulfonamide,
  (3E)-3-[(Dimethylamino)methylene]-1-(4-methoxydibenzo[b,d]furan-1-yl)-4-oxocyclohexanecarbonitrile,
  Ethyl 6-cyano-6-(4-methoxydibenzo[b,d]furan-1-yl)-2-methyl-5,6,7,8-tetrahydro quinoline-3-carboxylate,
  5-(4-Methoxydibenzo[b,d]furan-1-yl)-1-phenyl-4,5,6,7-tetrahydro-1H-indazole-5-carbonitrile,
  5-(4-Methoxydibenzo[b,d]furan-1-yl)-2-phenyl-4,5,6,7-tetrahydro-2H-indazole-5-carbonitrile,
  6-Cyano-6-(4-methoxydibenzo[b,d]furan-1-yl)-2-methyl-5,6,7,8-tetrahydro quinoline-3-carboxylic acid,
  5-(4Ethoxydibenzo[b,d]furan-1-yl)-4,5,6,7-tetrahydro-2,1-benzisoxazole-5-carbonitrile,
  5-(4-Methoxydibenzo[b,d]furan-1-yl)-3-oxo-3,3a,4,5,6,7-hexahydro-2H-indazole-5-carbonitrile,
  6-(4-Methoxydibenzo[b,d]furan-1-yl)-4-oxo-3,4,5,6,7,8-hexahydroquinazoline-6-carbonitrile,
  6-(4-Methoxydibenzo[b,d]furan-1-yl)-3-methyl-4-oxo-3,4,5,6,7,8-hexahydroquinazoline-6-carbonitrile,
  6-(4-Methoxydibenzo[b,d]furan-1-yl)-5,6,7,8-tetrahydroquinazoline-6-carbonitrile,
  2-Amino-6-(4-methoxydibenzo[b,d]furan-1-yl)-4-oxo-3,4,5,6,7,8-hexahydroquinazoline-6-carbonitrile,
  2-Amino-6-(4-methoxydibenzo[b,d]furan-1-yl)-5,6,7,8-tetrahydroquinazoline-6-carbonitrile,
  {[6-Cyano-6-(4-methoxydibenzo[b,d]furan-1-yl)-5,6,7,8-tetrahydroquinazolin-2-yl]amino}acetic acid,
  Ethyl [6-cyano-6-(4-methoxydibenzo[b,d]furan-1-yl)-4-oxo-5,6,7,8-tetrahydroquinazolin-3(4H)-yl]acetate,
  [6-Cyano-6-(4-methoxydibenzo[b,d]furan-1-yl)-4-oxo-5,6,7,8-tetrahydroquinazolin-3(4H)-yl]acetic acid,
  6-(4-Methoxydibenzo[b,d]furan-1-yl)-2-methyl-4-oxo-3,4,5,6,7,8-hexahydroquinazoline-6-carbonitrile, Ethyl [6-cyano-6-(4-methoxydibenzo[b,d]furan-1-yl)-2-methyl-4-oxo-5,6,7,8-tetrahydroquinazolin-3(4H)-yl] acetate, Ethyl {[6-cyano-6-(4-methoxydibenzo[b,d]furan-1-yl)-2-methyl-5,6,7,8-tetrahydroquinazolin-4-yl]oxy}acetate, 1-(4-Methoxydibenzo[b,d]furan-1-yl)-4-(methoxyimino) cyclohexanecarbonitrile, ({[4-Cyano-4-(4-methoxydibenzo[b,d]furan-1-yl)cyclohexylidene]amino}oxy)acetic acid and pharmaceutically acceptable salts thereof.

16. A compound according to claim 15, wherein the compound is Methyl-5-cyano-5-(4-methoxydibenzo[b,d]furan-1-yl)-2-oxocyclohexane carboxylate.

17. A compound according to claim 1 or a pharmaceutically acceptable salt thereof for use as a Phosphodiesterase 4 (PDE IV) inhibitor.

18. A compound according to claim 1 or a pharmaceutically acceptable salt thereof for use as a Phosphodiesterase 10 (PDE 10) inhibitor.

19. A pharmaceutical composition comprising, as an active ingredient, a compound according to claim 1 or a pharmaceutically acceptable salt thereof together with a pharmaceutically acceptable carrier or a diluent.

20. A process for preparing a compound according to claim 1 or a pharmaceutically acceptable salt, pharmaceutically acceptable enantiomer, diastereomer or N-oxide thereof comprising at least one of the steps a-e a. alkylating the compound of formula 3 wherein X is O, and Y is O

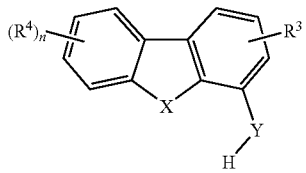

3 with a suitable alkylating agent to produce compound of formula 4

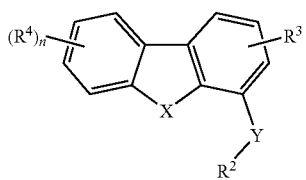

4 b. formulation of a compound of formula 4 using dichloromethyl methyl ether in the presence of a suitable Lewis acid to produce compound of formula 5

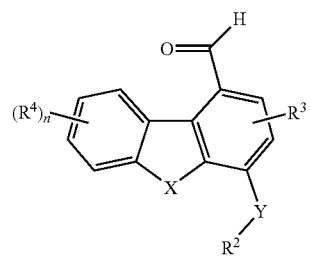

5 c. reduction of a compound of formula 5, followed by chlorination and cyanation to produce a compound of formula 6

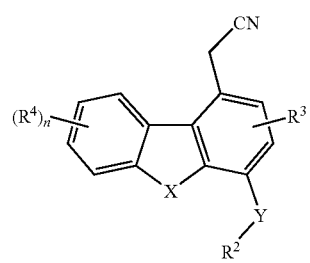

6 d. reaction of formula 6 with a suitable alkyl acrylate to form compound of formula 7

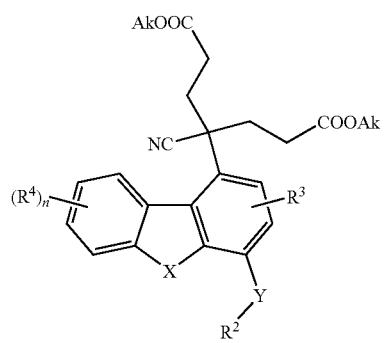

7 e. cyclisation and de-esterification of a compound of formula 7.

* * * * *